(12) United States Patent
Cohen et al.

(10) Patent No.: US 6,617,117 B1
(45) Date of Patent: Sep. 9, 2003

(54) MAP KINASES: POLYPEPTIDES, POLYNUCLEOTIDES AND USES THEREOF

(75) Inventors: Philip Cohen, Dundee (GB); Michel Goedert, Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/809,464

(22) Filed: Mar. 15, 2001

Related U.S. Application Data

(63) Continuation of application No. 09/284,090, filed as application No. PCT/GB97/02779 on Oct. 9, 1997, now abandoned.

(30) Foreign Application Priority Data

Oct. 9, 1996 (GB) .............................................. 9621096
May 15, 1997 (GB) .............................................. 9709781

(51) Int. Cl.[7] .............................................. G01N 33/53
(52) U.S. Cl. .......................... 435/7.1; 435/4; 435/7.91; 435/131; 435/194
(58) Field of Search ........................... 435/4, 7.1, 7.91, 435/131, 194

(56) References Cited

FOREIGN PATENT DOCUMENTS

| WO | WO94/21781 | 9/1994 |
|----|------------|--------|
| WO | WO96/36642 | 11/1996 |
| WO | WO97/02347 | 1/1997 |

OTHER PUBLICATIONS

Li et al. (1996) Biochem Biophys Res Comm 228(1662), 334–340.
Lechner et al. (1996) PNAS USA 93, 4355–4359.
Mertens et al (1996) FEBS Lett 383, 273–276.
Derijard et al. (1995) Science 267, 682–685.
Cuenda et al. (1996) EMBO J 15(16), 4156–4164.
Han et al. (1996) J Biol Chem 271(6), 2886–2891.
Goedert et al. (1997) EMBO J 16(12), 3563–3571.
Wang et al. (1997) J Biol Chem 272(38), 23668–23674.
Kumar et al. (1997) Biochem Biophys Res Comm 235, 533–538.
Cohen (1997) Trends Cell Biol 7, 353–361.
Cuenda et al. (1997) EMBO J 16(2), 295–305.
Sanchez et al. (1994) Nature 372, 794–798.
Yasher et al (1993) Mol Cell Biol 13, 5738–5748.
Doza et al (1995) FEBS Lett 364, 223–228.
Jiang et al (1996) J Biol Chem 271, 17920–17926.
Han et al. (1996) J Biol Chem 271, 2886–2891.
Moriguchi et al. (1996) J Biol Chem 271, 13675–13679.
Raingeaud et al. (1996) Mol Cell Biol 16, 1247–1255.
Stein et al. (1996) J Biol Chem 271, 11427–11433.
Meier et al. (1996) Eur J Biochem 236, 796–805.
Beyaert et al. (1996) EMBO J 15, 1914–1923.
Hazzalin et al. (1996) Curr Biol 6, 1028–1031.
Price et al. (1996) EMBO J 15, 6552–6563.

*Primary Examiner*—Francisco Prats
(74) *Attorney, Agent, or Firm*—Rogalskyj & Weyand, LLP

(57) ABSTRACT

The present invention relates to a method of identifying a compound which blocks the activation of a stress-activated protein kinase selected from the group consisting of SAPK4 and SAPK3 by SKK3. The method includes contacting the stress-activated protein kinase with the compound and determining whether the compound enhances or disrupts the interaction between the stress-activated protein kinase and SKK3. The invention further relates to a screening assay, a method of identifying agents able to influence the activity of a stress-activated protein kinase and a method of activating a stress-activated protein kinase.

10 Claims, 23 Drawing Sheets

Figure 3:
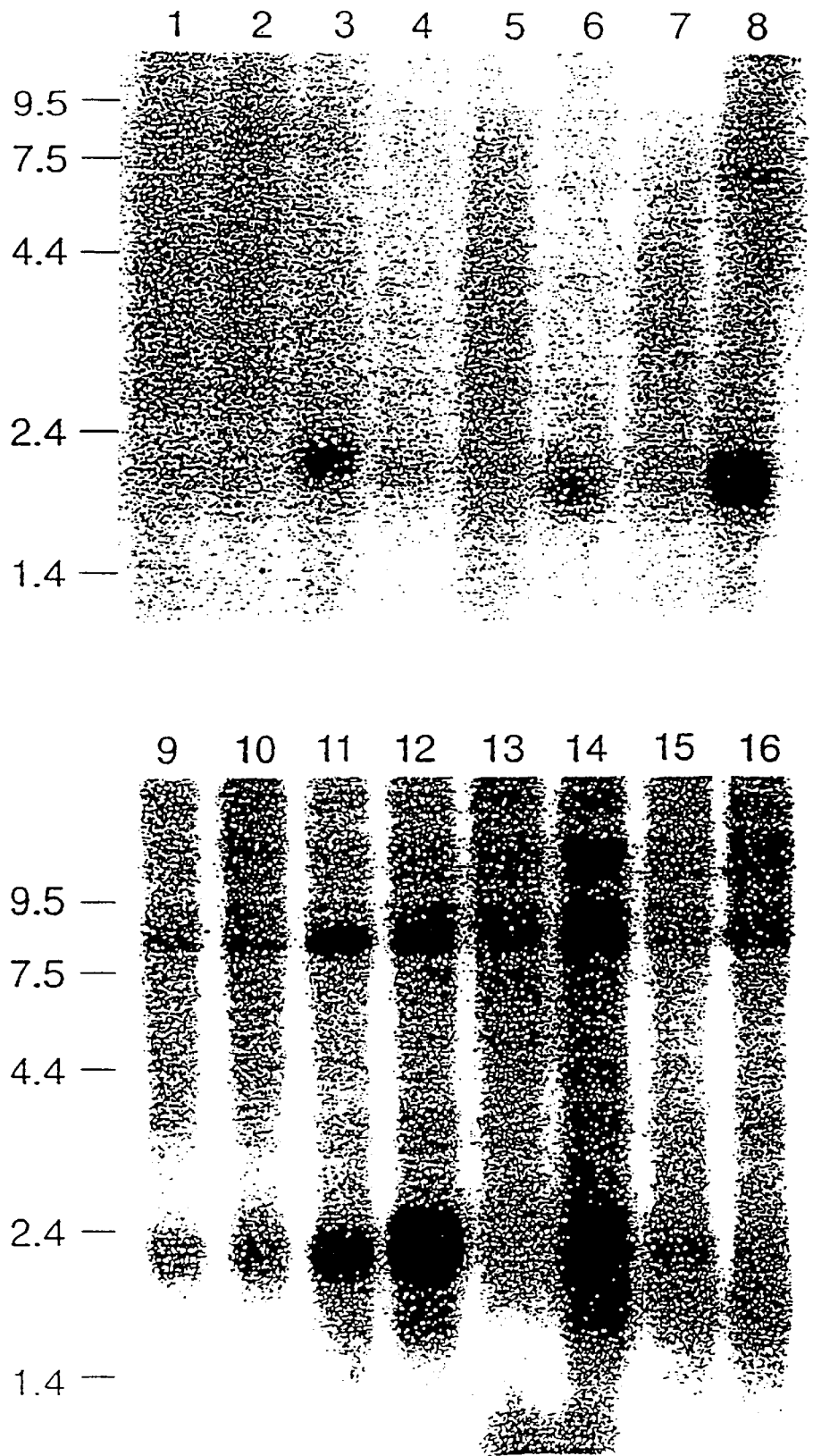

```
                                M   S   L   I   R   K   K   G   F   Y   K   Q   D    13
CCGCCGAGATCGGGTGCCCGGGATGAGCCTCATCCGGAAAAAGGGCTTCTACAAGCAGGA                              60

V   N   K   T   A   W   E   L   P   K   T   Y   V   S   P   T   H   V   G   S    33
CGTCAACAAGACCGCCTGGGAGCTGCCCAAGACCTACGTGTCCCCGACGCACGTCGGCAG                             120

G   A   Y   G   S   V   C   S   A   I   D   K   R   S   G   E   K   V   A   I    53
CGGGGCCTATGGCTCCGTGTGCTCGGCCATCGACAAGCGGTCAGGGGAGAAGGTGGCCAT                             180

K   K   L   S   R   P   F   Q   S   E   I   F   A   K   R   A   Y   R   E   L    73
CAAGAAGCTGAGCCGACCCTTTCAGTCCGAGATCTTCGCCAAGCGCGCCTACCGGGAGCT                             240

L   L   L   K   H   M   Q   H   E   N   V   I   G   L   L   D   V   F   T   P    93
GCTGCTGCTGAAGCACATGCAGCATGAGAACGTCATTGGGCTCCTGGATGTCTTCACCCC                             300

A   S   S   L   R   N   F   Y   D   F   Y   L   V   M   P   F   H   Q   T   D   113
AGCCTCCTCCCTGCGCAACTTCTATGACTTCTACCTGGTGATGCCCTTCATGCAGACGGA                             360

L   Q   K   I   M   G   M   E   F   S   E   E   K   I   Q   Y   L   V   Y   Q   133
TCTGCAGAAGATCATGGGGATGGAGTTCAGTGAGGAGAAGATCCAGTACCTGGTGTATCA                             420

M   L   K   G   L   K   Y   I   H   S   A   G   V   V   H   R   D   L   K   P   153
GATGCTCAAAGGCCTTAAGTACATCCACTCTGCTGGGGTCGTGCACAGGGACCTGAAGCC                             480

G   N   L   A   V   N   E   D   C   E   L   K   I   L   D   F   G   L   A   R   173
AGGCAACCTGGCTGTGAATGAGGACTGTGAACTGAAGATTCTGGATTTTGGGCTGGCGCG                             540

H   A   D   A   E   M   T   G   Y   V   V   T   R   W   Y   R   A   P   E   V   193
ACATGCAGACGCCGAGATGACTGGCTACGTGGTGACCCGCTGGTACCGAGCCCCCGAGGT                             600

I   L   S   W   M   H   Y   N   Q   T   V   D   I   W   S   V   G   C   I   M   213
GATCCTCAGCTGGATGCACTACAACCAGACAGTGGACATCTGGTCTGTGGGCTGTATCAT                             660

A   E   M   L   T   G   K   T   L   F   K   G   K   D   Y   L   D   Q   L   T   233
GGCAGAGATGCTGACAGGGAAAACTCTGTTCAAGGGGAAAGATTACCTGGACCAGCTGAC                             720

Q   I   L   K   V   T   G   V   P   G   T   E   F   V   Q   K   L   N   D   K   253
CCAGATCCTGAAAGTGACCGGGGTGCCTGGCACGGAGTTTGTGCAGAAGCTGAACGACAA                             780

A   A   K   S   Y   I   Q   S   L   P   Q   T   P   R   K   D   F   T   Q   L   273
AGCGGCCAAATCCTACATCCAGTCCCTGCCACAGACCCCCAGGAAGGATTTCACTCAGCT                             840

F   P   R   A   S   P   Q   A   A   D   L   L   E   K   M   L   E   L   D   V   293
GTTCCCACGGGCCAGCCCCCAGGCTGCGGACCTGCTGGAGAAGATGCTGGAGCTAGACGT                             900

D   K   R   L   T   A   A   Q   A   L   T   H   P   F   F   E   P   F   R   D   313
GGACAAGCGCCTGACGGCCGCGCAGGCCCTCACCCATCCCTTCTTTGAACCCTTCCGGGA                             960

P   E   E   E   T   E   A   Q   Q   P   F   D   D   S   L   E   H   E   K   L   333
CCCTGAGGAAGAGACGGAGGCCCAGCAGCCGTTTGATGATTCCTTAGAACACGAGAAACT                            1020

T   V   D   E   W   K   Q   H   I   Y   K   E   I   V   N   F   S   P   I   A   353
CACAGTGGATGAATGGAAGCAGCACATCTACAAGGAGATTGTGAACTTCAGCCCCATTGC                            1080

R   K   D   S   R   R   R   S   G   M   K   L   *               365
CCGGAAGGACTCACGGCGCCGGAGTGGCATGAAGCTGTAGGGACTCATCTTGCATGGCAC                            1140

CGCCGGCCAGACACTGCCCAAGGACCAGTATTTGTCACTACCAAACTCAGCCCTTCTTGG .                          1200

AATACAGCCTTTCAAGCAGAGGACAGAAGGGTCCTTCTCCTTATGTGGGAAATGGGCCT                             1259
```

Figure 1

```
SAPK4   MSLIRKKGFYKQDVNKTAMELRKTVVSP           28
SAPK3   MSSPPPARSGFYRQEVTKTAWEVRAVVRDL         30
SAPK2b  MSGPRAGFYRQELNKTVWEVPQRLQGL            27
SAPK2a  MSQERPTFYRQELNKTIWEVPERYQNL            27
HOG1    MTTNEEFIRTQIFGTVFEITNRYNDL             26

SAPK4   THVGSGAYGSVCSALDKRSGEKVAIKKLSR         58
SAPK3   QPVGSGAYGAVCSAVDGRTGAKVAIKKLYR         60
SAPK2b  RPVGSGAYGSVCSAYDARLRQKVAVKKLSR         57
SAPK2a  SPVGSGAYGSVCAAFDTKTGLRVAVKKLSR         57
HOG1    NPVGMGAFGLVCSATDTLTSQPVAIKKIMK         56

SAPK4   PFQSEIFAKRAYRELLLLKHMQHENVIGLL         88
SAPK3   PFQSELFAKRAYRELRLLKHMRHENVIGLL         90
SAPK2b  PFQSLIHARRTYRELRLLKHLKHENVIGLL         87
SAPK2a  PFQSIIHAKRTYRELRLLKHMKHENVIGLL         87
HOG1    PFSTAVLAKRTYRELKLLKHLRHENLICLQ         86

SAPK4   DVFTPASSLRNFYDFYLVMPFMQTDLQKIM         118
SAPK3   DVFTPDETLDDFTDFYLVMPFMGTDLGKLM         120
SAPK2b  DVFTPATSIEDFSEVYLVTLMGADLNNIV          117
SAPK2a  DVFTPARSLEEFNDVYLVTHLMGADLNNIV         117
HOG1    DIF-----LSPLEDIYFVTELQGTDLHRLL         111

SAPK4   GMEF-SEEKIQYLVYQMLKGLKYIHSAGVV         147
SAPK3   KHEKLGEQRIQFLVYQMLKGLRYIHAAGII         150
SAPK2b  KCQALSDEHVQFLVYQLLRGLKYIHSAGII         147
SAPK2a  KCQKLTDDHVQFLIYQILRGLKYIHSADII         147
HOG1    QTRPLEKQFVQYFLYQILRGLKYVHSAGVI         141

SAPK4   HRDLKPGNLAVNEDCELKILDFGLARHADA         177
SAPK3   HRDLKPGNLAVNEDCELKILDFGLARQADS         180
SAPK2b  HRDLKPSNVAVNEDCELRILDFGLARQADE         177
SAPK2a  HRDLKPSNLAVNEDCELKILDFGLARHTDD         177
HOG1    HRDLKPSNILINENCDLKICDFGLARIQDP         171
              * *
SAPK4   EMTGYVVTRWYRAPEVILSWMHYNQTVDIW         207
SAPK3   EMTGYVVTRWYRAPEVILNWMRYTQTVDIW         210
SAPK2b  EMTGYVATRWYRAPEIMLNWMHYNQTVDIW         207
SAPK2a  EMTGYVATRWYRAPEIMLNWMHYNQTVDIW         207
HOG1    QMTGYVSTRYYRAPEIMLTWQKYDVEVDIW         201

SAPK4   SVGCIMAEMLTGKTLFKGKDYLDQLTQILK         237
SAPK3   SVGCIMAEMITGKTLFKGSDHLDQLKEIMK         240
SAPK2b  SVGCIMAELQSKALFPGSDYIDQLKRIME          237
SAPK2a  SVGCIMAELLTGRTLFPGTDHIDQLKLILR         237
HOG1    SAGCIFAEMIEGKPLFPGKDHVHQFSIITD         231

SAPK4   VTGVPGTEFVQKLNDKAAKSYIQSLPQTPR         267
SAPK3   VTGTPPAEFVQRLQSDEAKNYMKGLPELEK         270
SAPK2b  VVGTPSPEVLAKISSEHARTYIQSLPPMPQ         267
SAPK2a  LVGTPGAELLKKISSESARNYIQSLTQMPK         267
HOG1    LLSSPPKDVINTICSENTLKFVTSLPHRDP         261

SAPK4   KDFTQLFPRASFQAADLLEKMLELDVDKRL         287
SAPK3   KDFASILTNASPLAVNLLEKMLVLDAEQRV         300
SAPK2b  KDLSSIFRGANPLAIDLLGRMLVLDSDQRV         297
SAPK2a  MNFANVFIGANPLAVDLLEKMLVLDSDKRI         297
HOG1    IPFSERFKTVEPDAVDLLEKMLVFDPKKRI         291

SAPK4   TAAQALIHPFFEPFRDPEEETEAQQPFDDS         327
SAPK3   TAGEALAHPYFESLHDTEDEPQV-QKYDDS         329
SAPK2b  SAAEALAHAYFSQYHDPEDEPEA-EPYDES         326
SAPK2a  TAAQALAHAYFAQYHDPDDEPVA-DPYDQS         321
HOG1    TAADALAHPYSAPYHDPTDEPVADKFDWH          321

SAPK4   LEHEKLTVDEWKQHIYKEIVNFSPIARKDS         357
SAPK3   FDDVDRTLDEWKRVTYKEVLSFKPPRQLGA         359
SAPK2b  VEAKERTLEEWKELTYQEVLSFKPPEPPKP         356
SAPK2a  FESRDLLIDEWKSLTYQEVISFVPPPLDQE         356
HOG1    FNDADLPVDTWRVMMYSEILDFHKIGGSDG         351

SAPK4   RRRSGMKL                               365
SAPK3   RVSKETPL                               367
SAPK2b  PGSLEIEQ                               364
SAPK2a  EMES                                   360
HOG1    QIDISATFDDQVAAATAAAAQAQAQAQAQV         381

HOG1    QLNMAAHSHNGAGTTGNDHSDIAGGNKGQH         411

HOG1    SCSCK                                  416
```

Figure 2

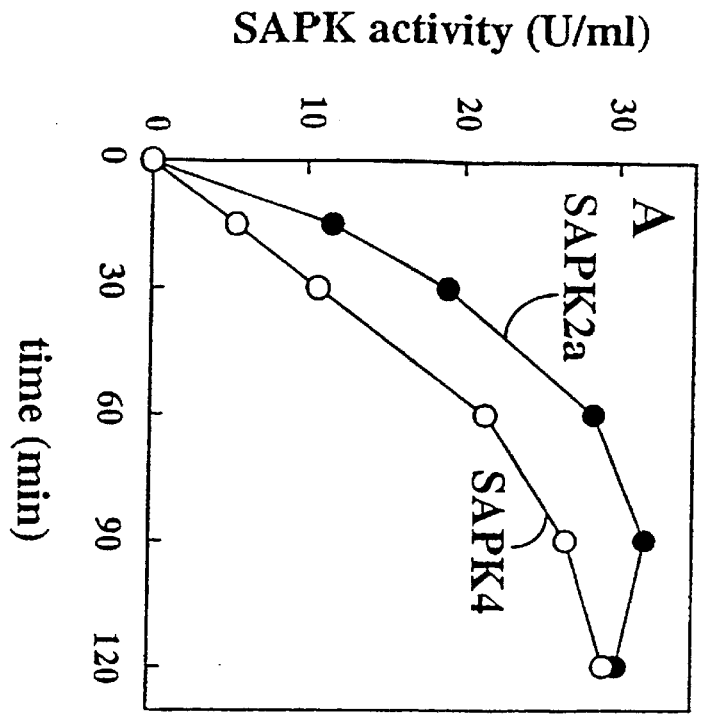
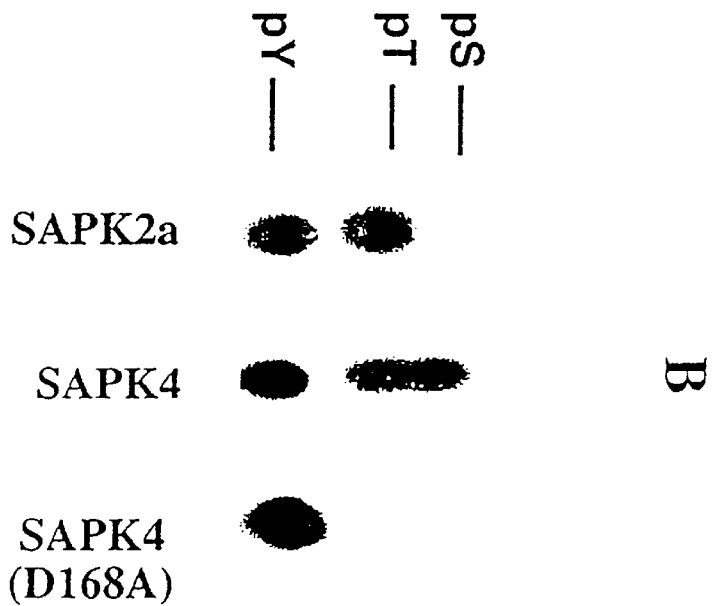
Figure 6

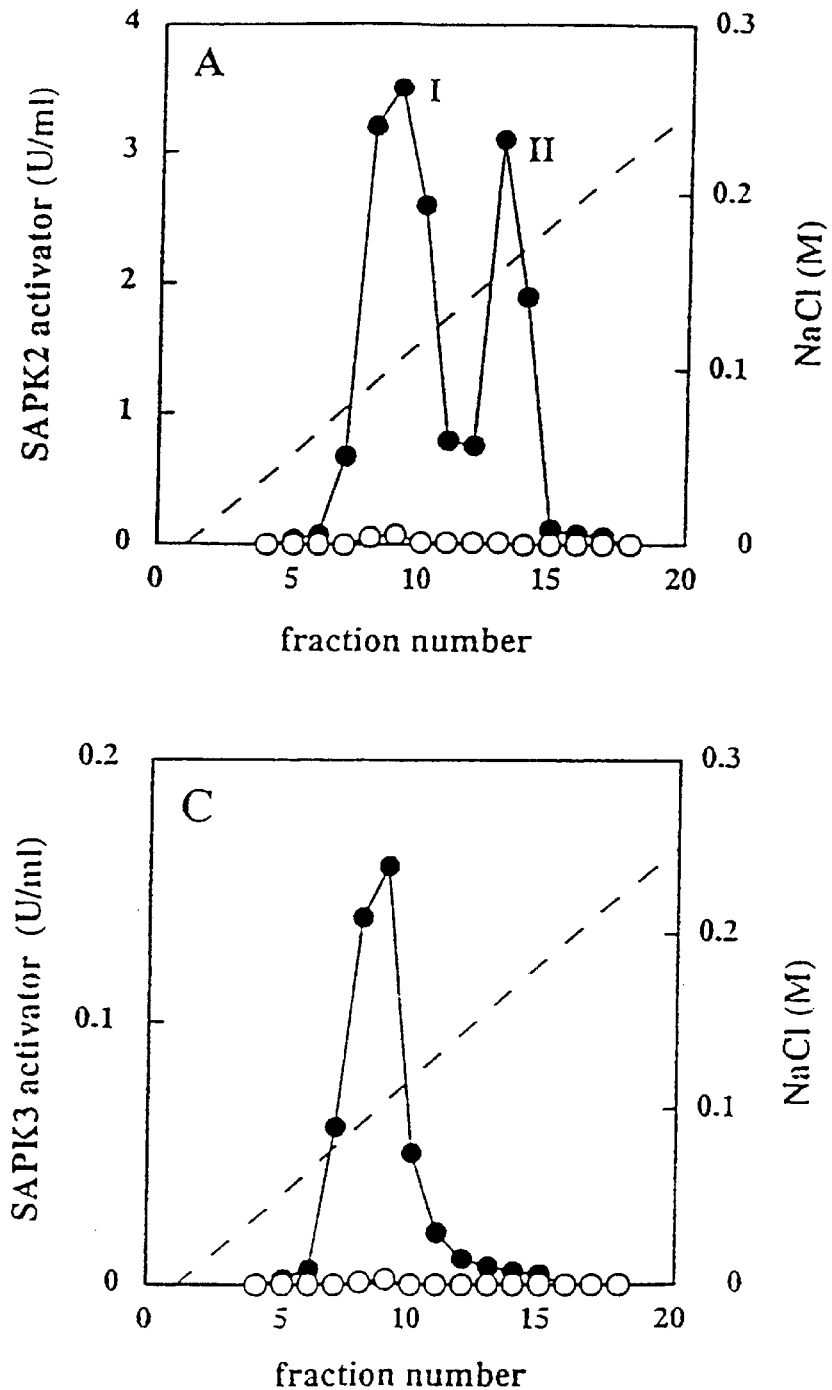
Figure 12 (page 1 of 2)

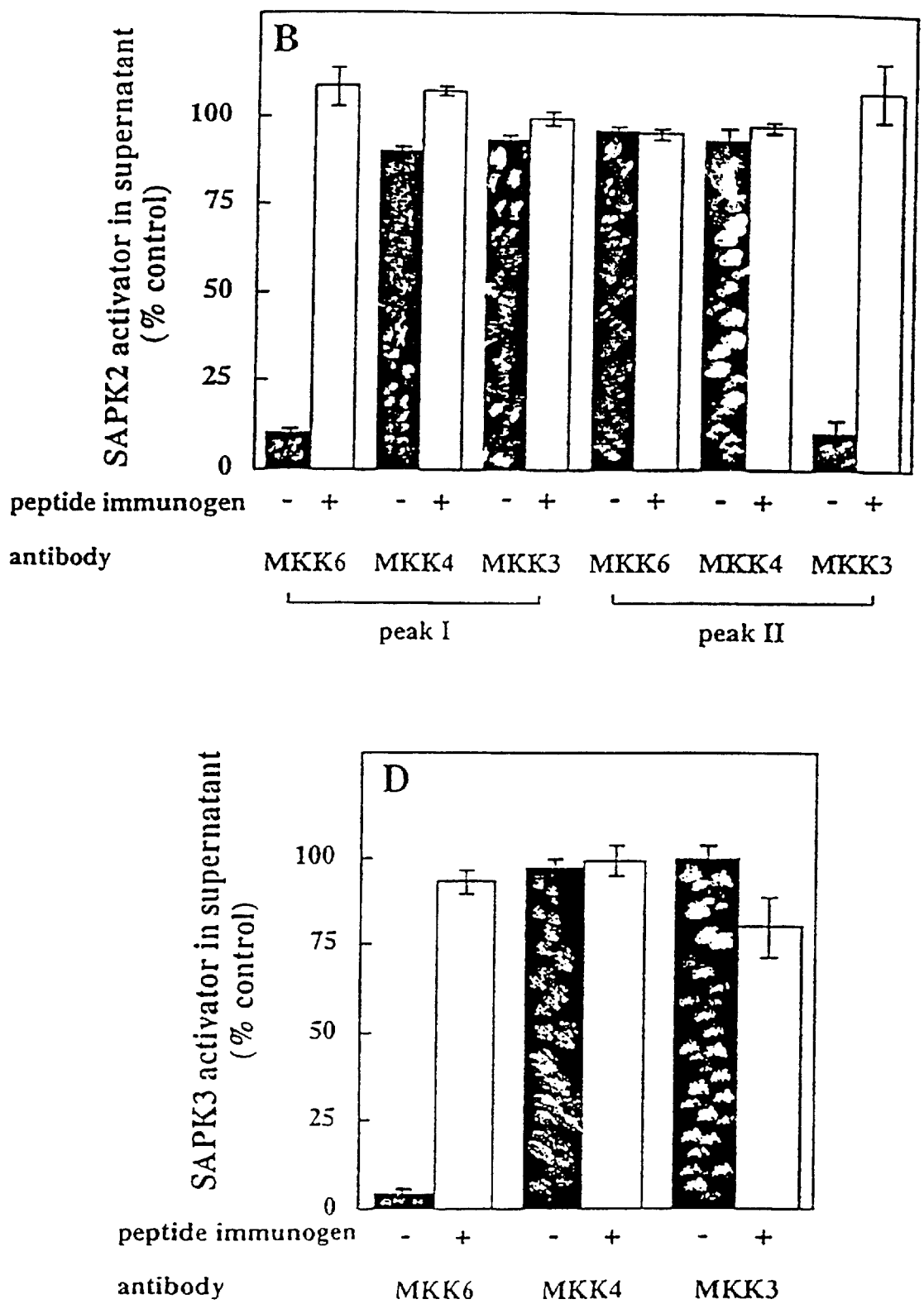
Figure 12 (page 2 of 2)

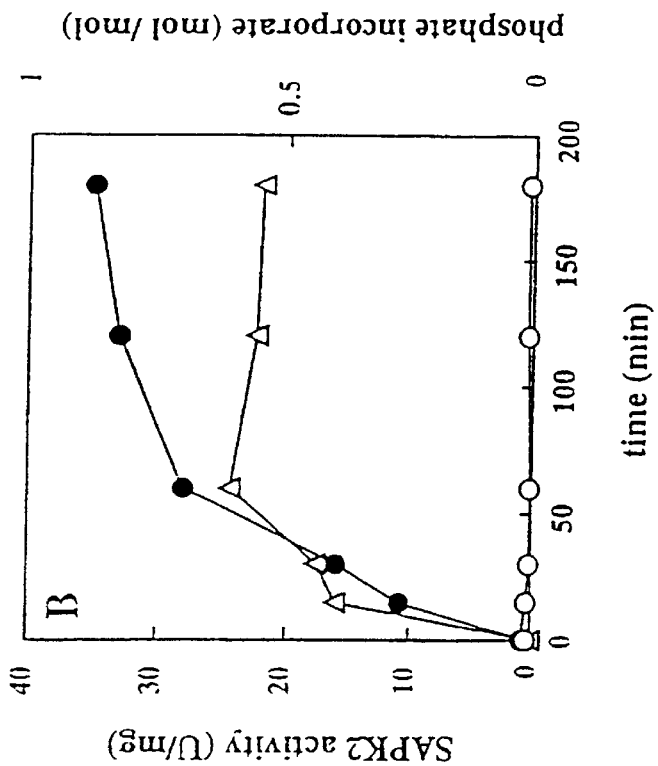
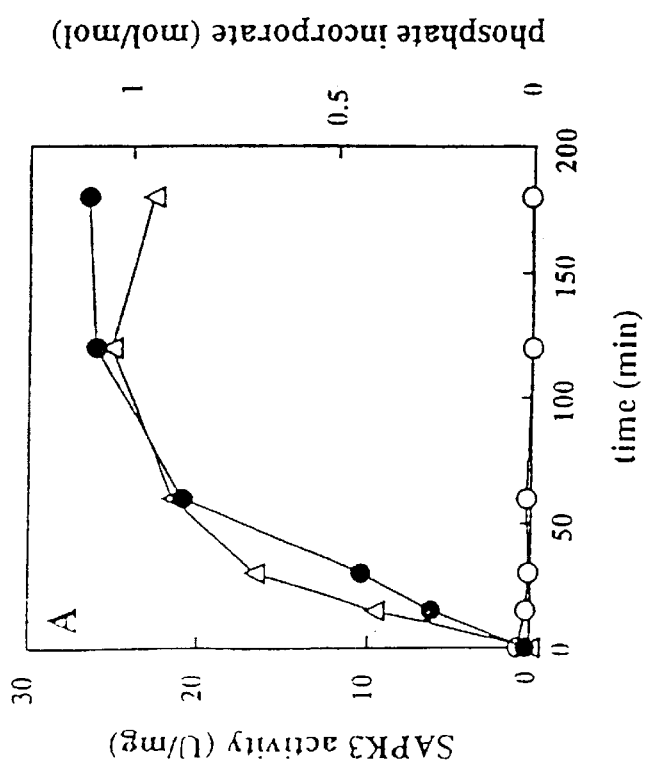
Figure 15 (page 1 of 2)

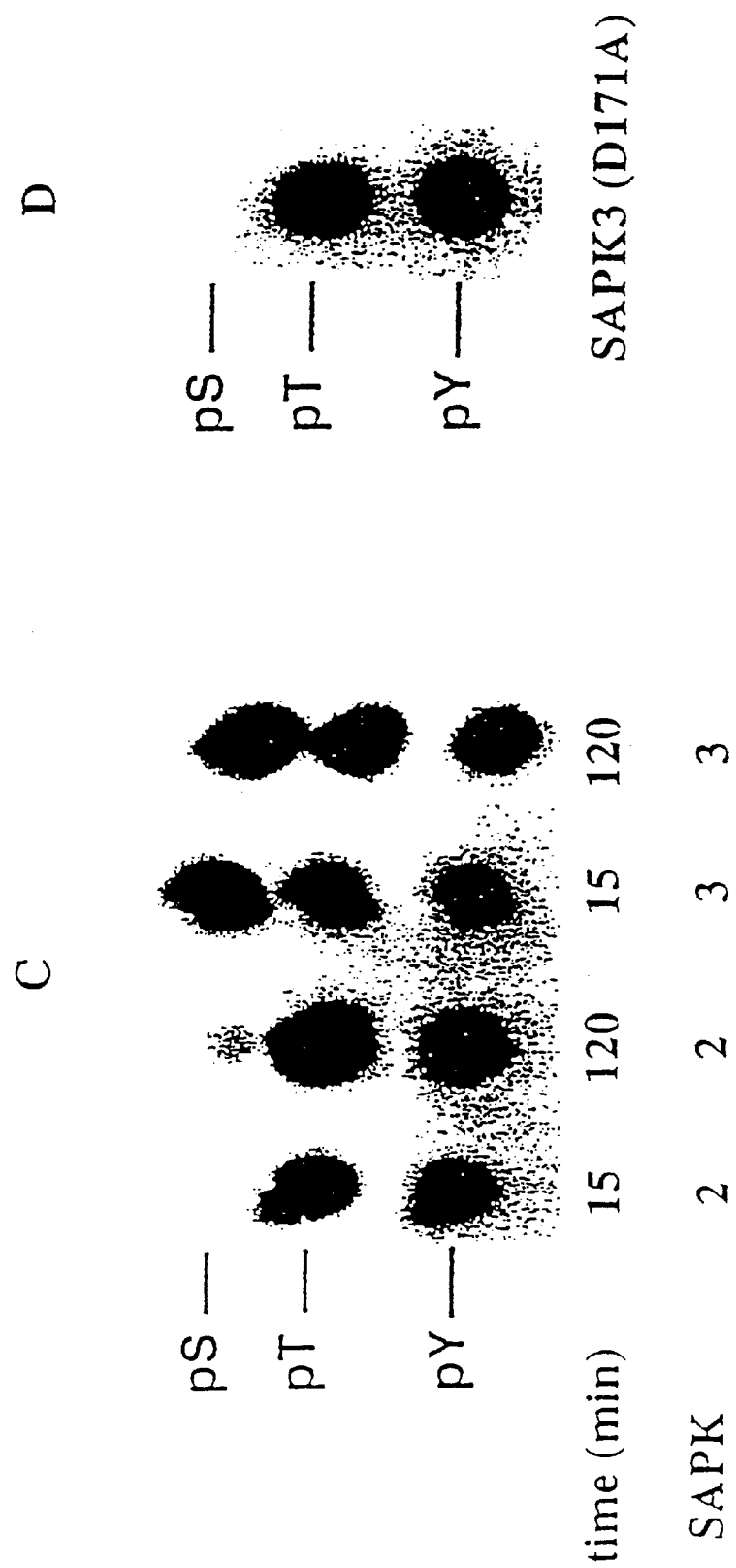
Figure 15 (page 2 of 2)

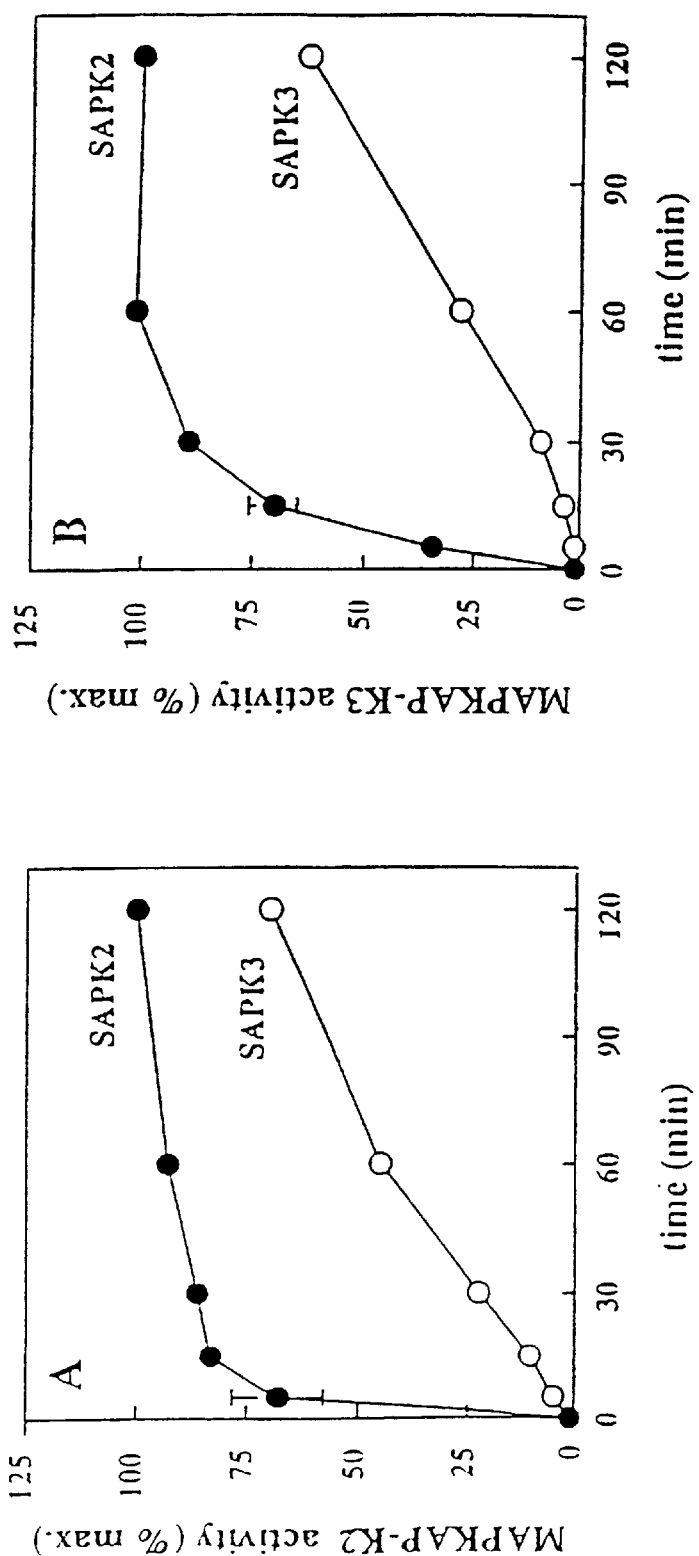
Figure 18 (page 1 of 2)

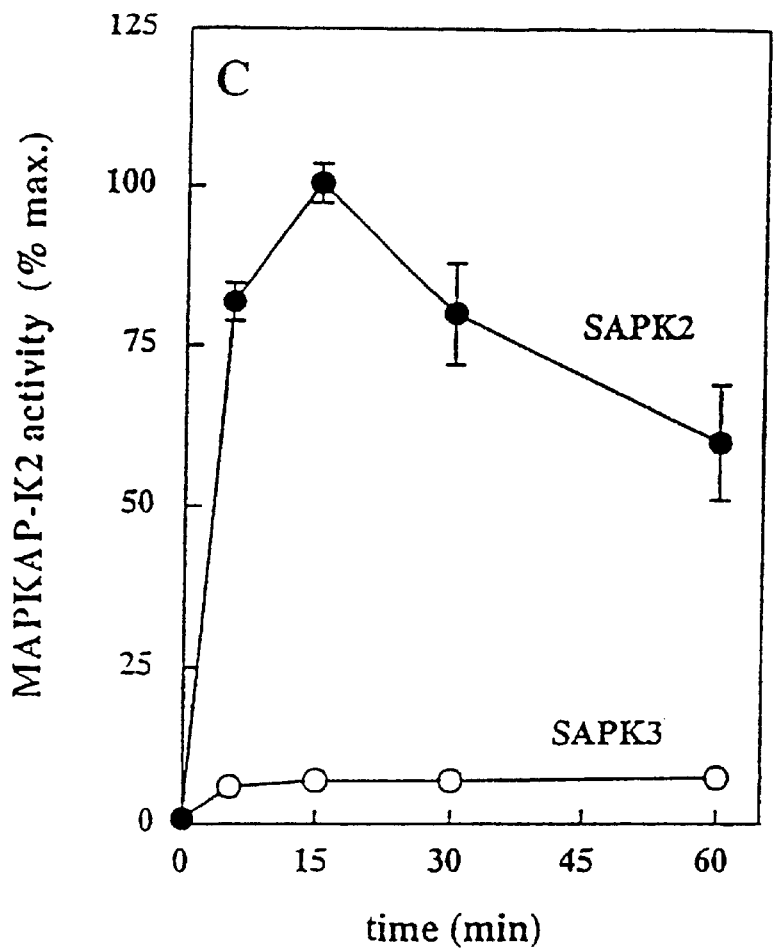
Figure 18 (page 2 of 2)

MAP KINASES: POLYPEPTIDES, POLYNUCLEOTIDES AND USES THEREOF

This application is a continuation of U.S. patent application Ser. No. 09/284,090 filed Jun. 28, 1999 now abandoned based on PCT/GB97/02779, filed Oct. 9, 1997.

The present invention relates to polypeptides, polynucleotides and uses thereof, in particular to members of the stress-activated protein kinase (SAPK) family.

Four mitogen-activated protein (MAP) kinase family members are activated by cellular stresses (chemical, heat and osmotic shock, ultraviolet radiation, inhibitors of protein synthesis), bacterial lipopolysaccharide (LPS), and the cytokines interleukin-1 (IL1) and tumour necrosis factor (TNF), and have therefore been termed stress-activated protein kinases or SAPKs (reviewed in Cohen, 1997). Isoforms of SAPK1 [also called c-Jun N-terminal kinases (JNKs)] phosphorylate Ser-63 and Ser-73 in the activation domain of c-Jun (Pulverer et al, 1991), thereby increasing its transcriptional activity. The transcription factors Elk1 (Cavigelli et al, 1995 and ATF2 are phosphorylated in vitro (the latter at Thr-69, Thr-71, and Ser-90 (Gupta et al, 1995; Livingstone et al, 1995), increasing the transcriptional activity of these proteins. The same sites in the transcription factor c-Jun also become phosphorylated when cells are exposed to the stresses and cytokines that activate SAPK1, or after cotransfection with protein kinases known to activate SAPK1 (Pulverer et al, 1991; Hibi et al, 1993; Dérijard et al, 1994; Kyriakis et al, 1994; Cavigelli et al, 1995; Gupta et al, 1995; Whitmarsh et al, 1995; Zinck et al, 1995), suggesting that c-Jun is a physiological substrate for SAPK1.

SAPK2a [also termed p38 (Han et al, 1994), p40 (Freshney et al, 1994), RK (Rouse et al, 1994), CSBP (Lee et al, 1994) and Mxi2 (Zervos et al, 1995)] is inhibited very specifically by the pyridinyl imidazoles SB 203580 and SB 202190 (Lee et al, 1994; Cuenda et al., 1995; reviewed in Cohen, 1997) which have been exploited to identify several physiological substrates. These include four protein kinases, namely MAP kinase-activated protein kinase-2 (MAPKAP-K2, Rouse et al, 1994) and the closely related MAPKAP-K3, which shares 75% amino acid sequence identity and has similar substrate specificity in vitro (McLaughlin et al, 1996; Ludwig et al, 1996; Clifton et al, 1996), as well as MAP kinase interacting protein kinases-1 and -2 (Mnk1 and Mnk2) (Waskiewicz et al, 1997; Fukunaga and Hunter, 1997).

Physiological substrates of MAPKAP-K2/K3 include heat shock protein (HSP) 27 (Stokoe et al, 1992a; Cuenda et al, 1995; Huot et al, 1995) and the transcription factor CREB (Tan et al, 1996), whereas transcription factor eIEF4E is a physiological substrate of Mnk1/2 (Waskiewicz et al, 1997). The phosphorylation of HSP27 appears to enhance the polymerisation of actin and is thought to help repair the actin microfilament network which becomes disrupted during cellular stress, thereby aiding cell survival (Lavoie et al, 1995). The phosphorylation of CREB (at Ser-133) is essential to allow this protein to stimulate the ascription of genes that contain cyclic AMP response elements (CREs). SAPK2a also mediates the stress-induced phosphorylation (at Ser-78 and Ser-81) and activation of the CEBPβ-related transcription factor CHOP (Wang and Ron, 1996) and the ternary complex factor Elk-1 (Price et al, 1996).

Based on the effects of SB 203580, the activation of SAPK2a is rate-limiting in the LPS-induced production of IL1 and TNF in monocytes (Lee et al, 1994), in the TNF-stimulated transcription of IL6 and GM-CSF in fibroblasts (Beyaert et al, 1996), in the IL1-induced stimulation of glucose uptake in epithelial cells (Gould et al, 1995), in collagen-induced platelet aggregation (Saklatvala et al, 1996), in the stress-induced transcription of c-Jun and c-Fos in fibroblasts (Hazzalin et al, 1996; Price et al, 1996) and in the LPS-induced synthesis of cyclo-oxygenase-2 (COX-2, the rate limiting enzyme in prostaglandin synthesis) in RAW264.7 macrophages (Paul et al 1996). Since the c-fos and COX2 promoters contain CREs, the MAPKAP-K2/K3 mediated phosphorylation of CREB may contribute to the stress and cytokine-induced transcription of these two genes The importance of the CRE in the induction of c-fos mRNA is well documented (Ginty et al 1994). The SAPK2a catalysed phosphorylation of Elk-1 (Price et al, 1996) and the MAPKAP-K2 catalysed phosphorylation of CREB (Tan et al, 1996) are both likely to contribute to the stress-induced transcription of c-fos (Ginty et al, 1994). The transcription factors ATF2 and Elk-1 are also phosphorylated by SAPK2 in vitro and after transfection of mammalian cells with the upstream activators of SAPK2 that do not activate SAPK1 (Raingeaud et al, 1996).

Recently, two additional SAP kinases were identified, called SAPK2b [or p38β (Jiang et al, 1996)] and SAPK3 (Mertens et al, 1996) [also called ERK6 (Lechner et al, 1996) and p38γ (Li et al, 1996)]. The amino acid sequence of SAPK2b is 73% identical to SAPK2a and it is inhibited by SB 202190 at similar concentrations to SAPK2a. In contrast, the amino acid sequence of SAPK3 is only 60% identical to SAPK2a and SAPK2b and 47% identical to SAPK1. Like SAPK2, SAPK3 contains a TGY motif in the activation domain (which is TPY in SAPK1 and TEY in p42 and p44 MAP kinases) and subdomain VII is separated by six amino acids from the activation loop in subdomain VIII (as compared to eight residues in SAPK1 and >12 residues in any other MAP kinase family member). SAPK2b has been introduced into mammalian cells by transient transfection and shown to be activated in response to pro-inflammatory cytokines and stressful stimuli in a manner similar to SAPK1 and SAPK2a. The physiological roles of SAPK2b and SAPK3 are unknown. The mRNAs encoding these enzymes are present in all mammalian tissues examined (Jiang et al, 1996; Mertens et al, 1996; Goedert et al., 1997), with the mRNA encoding SAPK3 being highest in skeletal muscle. Expression of wild-type SAPK3 and an inactive mutant in the muscle cell line C2C12 enhanced and inhibited differentiation into myotubes, respectively (Lechner et al, 1996). In vitro, SAPK2b and SAPK3 phosphorylated several proteins that are also substrates for SAPK2a. SAPK2b was reported to phosphorylate the transcription factor ATF2 more efficiently than SAPK2a (Jiang et al., 1996) but, since the stress- and cytokine-induced phosphorylation of ATF2 in fibroblasts is unaffected by SB 203580 (Hazzalin et al., 1996; Beyaert et al., 1996), neither SAPK2a nor SAPK2b appears to be rate-limiting for ATF2 phosphorylation in vivo, in contrast to earlier studies using transfection-based approaches (Gupta et al, 1995). However, whether SAPK1 and/or SAPK3 are rate-limiting for ATF2 phosphorylation in vivo is unknown.

Five chromatographically distinct SAP kinase kinases (SKKs or SAPKKs) have been identified in mammalian cells (Meier et al, 1996; Cuenda et al, 1996). In vitro, SKK1 [also termed MKK4 (Dérijard et al, 1995), SEK1 (Sanchez et al, 1994) and XMEK2 (Yashar et al, 1993)] activates all four SAPKs 1, 2a and 2b (Sanchez et al, 1994; Dérijard et al, 1995; Doza et al, 1995; Jiang et al, 1996), although SAPK2b is phosphorylated less efficiently. SKK2 [also termed MKK3 (Dérijard et al, 1995)] and SKK3 (Cuenda et al, 1996) [also called MKK6 (Han et al, 1996; Moriguchi et al, 1996; Raingeaud et al, 1996) and MEK6 (Stein et al, 1996)] activate SAPK2a but not SAPK1. SKK3 was also the most efficient activator of SAPK2b in co-transfection experiments (Jiang et al, 1996). SKK4 and SKK5 activate SAPK1 but not SAPK2a (Meier et al, 1996). SKK4/SKK5 have not been purified or cloned and their amino acid sequences are thus still unknown. SKK1 and SKK2 are the only activators of SAPK2 generated when rat pheochromocytoma (PC12) cells are exposed to chemical stress, osmotic shock, ultraviolet irradiation or the protein synthesis inhibitor anisomycin (Meier et al, 1996). However, SKK3 is the dominant activator of SAPK2 and SKK4/SKK5 is/are the dominant activator(s) of SAPK1 when human epithelial (KB) cells are exposed to the same stresses as PC12 cells or stimulated with IL-1, or when human (THP1) monocytes are stimulated with LPS (Meier et al, 1996; Cuenda et al, 1996). The identity of the upstream activators of SAPK1 and SAPK2 may therefore vary from cell to cell.

At least five enzymes capable of activating SKK1, SKK2 and SKK3 in vitro and/or in cotransfection experiments have been identified, namely MEK kinase (MEKK) (Yan et al, 1994; Lin et al, 1995; Matsuda et al, 1995; Blank et al, 1996), MAP kinase upstream kinase (MUK) (Hirai et al, 1996), mixed lineage kinase-3 (MLK3) (Rana et al, 1996), TGFb-activated protein kinase-1 (TAK-1) (Moriguchi et al, 1996) and the protooncogene Tp12 (Salmeron et al, 1996) MEKK activates cotransfected SAPK1 more effectively than cotransfected SAPK2 or MAP kinase kinase-1 (MKK1, a physiological activator of p42 and of 44 MAP kinases) (Xu et al,1996). However, SKK1 can also be activated by MUK, MLK3 and Tp12, SKK2 by TAK1, while Tp12 can also activate MAPKK1. Further work is needed to understand which (if any) of these kinases activate each SAPKK in vivo under different conditions.

We here report the cloning of a novel MAP kinase family member that we call SAPK4, and characterisation of SAPK3 and SAPK4. SAPK4, which also contains a TGY sequence in the activation domain, shows about 60% identity to SAPK2a, SAPK2b and SAPK3 and its mRNA is widely expressed in human tissues. We show that SAPK4 is activated by the same stimuli that activate other SAP kinases and that SKK3 is likely to be the major upstream activator of SAPK3 and SAPK4 in vivo. The substrate specificity of SAPK4 in vitro is similar to that of SAPK3 and neither SAPK3 nor SAPK4 are inhibited by SB 203580 or SB 202190.

A first aspect of the invention provides a substantially pure stress-activated protein kinase comprising the amino acid sequence identified as SEQ. ID. NO: 1.

```
M S L I R K K G F Y K Q D V N K T A W E
L P K T Y V S P T H V G S G A Y G S V C
S A I D K R S G E K V A I K K L S R P F
Q S E I F A K R A Y R E L L L L K H M Q
H E N V I G L L D V F T P A S S L R N F
Y D F Y L V M P F M Q T D L Q K I M G M
E F S E E K I Q Y L V Y Q M L K G L K Y
I H S A G V V H R D L K P G N L A V N E
D C E L K I L D F G L A R H A D A E M T
G Y V V T R W Y R A P E V I L S W M H Y
N Q T V D I W S V G C I M A E M L T G K
T L F K G K D Y L D Q L T Q I L K V T G
V P G T E F V Q K L N D K A A K S Y I Q
S L P Q T P R K D F T Q L F P R A S P Q
A A D L L E K M L E L D V D K R L T A A
Q A L T H P F F E P F R D P E E E T E A
Q Q P F D D S L E H E K L T V D E W K Q
H I Y K E I V N F S P I A R K D S R R R
S G M K L,
``` or a variant, fragment, fusion or derivative thereof, or a fusion of a said variant or fragment or derivative.

The polypeptide with the amino acid sequence as shown above is herein referred to as SAPK4 (stress-activated protein kinase 4).

By "substantially pure" we mean that the said protein kinase is substantially free of other proteins. Thus, we include any composition that includes at least 30% of the protein content by weight as the said protein kinase, preferably at least 50%, more preferably at least 70%, still more preferably at least 90% and most preferably at least 95% of the protein content is the said protein kinase.

Thus, the invention also includes compositions comprising the said protein kinase and a contaminant wherein the contaminant comprises less than 70% of the composition by weight, preferably less than 50% of the composition, more preferably less than 30% of the composition, still more preferably less than 10% of the composition and most preferably less than 5% of the composition by weight.

The invention also includes the substantially pure said protein kinase when combined with other components ex vivo, said other components not being all of the components found in the cell in which said protein kinase is found.

By "variants" of the polypeptide we include insertions, deletions and substitutions, either conservative or non-conservative. In particular we include variants of the polypeptide where such changes do not substantially alter the activity of the said protein kinase.

By "conservative substitutions" is intended combinations such as Gly, Ala; Val, Ile, Leu; Asp, Glu; Asn, Gln; Ser, Thr; Lys, Arg; and Phe, Tyr.

It is particularly preferred if the stress-activated protein kinase variant has an amino acid sequence which has at least 65% identity with the amino acid sequence given above, more preferably at least 70%, still more preferably at least 75%, yet still more preferably at least 80%, in further preference at least 85%, in still further preference at least 90% and most preferably at least 95% or 97% identity with the amino acid sequence given above.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

A particular embodiment of the invention provides a substantially pure human SAPK4 polypeptide which consists of the amino acid sequence identified as SEQ. ID. NO: 1.

```
M S L I R K K G F Y K Q D V N K T A W E
L P K T Y V S P T H V G S G A Y G S V C
S A I D K R S G E K V A I K K L S R P F
Q S E I F A K R A Y R E L L L L K H M Q
H E N V I G L L D V F T P A S S L R N F
Y D F Y L V M P F M Q T D L Q K I M G M
E F S E E K I Q Y L V Y Q M L K G L K Y
I H S A G V V H R D L K P G N L A V N E
D C E L K I L D F G L A R H A D A E M T
G Y V V T R W Y R A P E V I L S W M H Y
N Q T V D I W S V G C I M A E M L T G K
T L F K G K D Y L D Q L T Q I L K V T G
V P G T E F V Q K L N D K A A K S Y I Q
S L P Q T P R K D F T Q L F P R A S P Q
A A D L L E K M L E L D V D K R L T A A
Q A L T H P F F E P F R D P E E E T E A
Q Q P F D D S L E H E K L T V D E W K Q
H I Y K E I V N F S P I A R K D S R R R
S G M K L,
``` or naturally occurring allelic variants thereof.

It is particularly preferred, although not essential, that the variant or fragment or derivative or fusion of the said protein kinase, or the fusion of the variant or fragment or derivative has at least 30% of the enzyme activity of SAPK4 with respect to the phosphorylation of myelin basic protein. It is more preferred if the variant or fragment or derivative or fusion of the said protein kinase, or the fusion of the variant or fragment or derivative has at least 50%, preferably at least 70% and more preferably at least 90% of the enzyme activity of SAPK4 with respect to the phosphorylation of myelin basic protein. However, it will be appreciated that variants or fusions or derivatives or fragments which are devoid of enzymatic activity may nevertheless be useful, for example by interacting with another polypeptide.

A second aspect of the invention provides a recombinant polynucleotide encoding a protein kinase as defined in the first aspect of the invention or encoding a variant or fragment or derivative of fusion of said kinase or a fusion of a said variant or fragment or derivative. Preferences for the said protein kinase variant are the same as in the first aspect of the invention.

In one preferred embodiment the polynucleotide comprises the nucleotide sequence identified as SEQ. ID. NO: 2 as follows.

bind to the protein encoded by the said polynucleotide or (ii) an antisense sequence corresponding to the gene or to a variation of type (i) as just defined. For example, different codons can be substituted which code for the same amino acid(s) as the original codons. Alternatively, the substitute codons may code for a different amino acid that will not affect the activity or immunogenicity of the protein or which may improve or otherwise modulate its activity or immunogenicity. For example, site-directed mutagenesis or other techniques can be employed to create single or multiple mutations, such as replacements, insertions, deletions, and transpositions, as described in Botstein and Shortle; "Strategies and Applications of In Vitro Mutagenesis," *Science*, 229: 193–210 (1985), which is incorporated herein by reference. Since such modified polynucleotides can be obtained by the application of known techniques to the teachings contained herein, such modified polynucleotides are within the scope of the claimed invention.

Moreover, it will be recognised by those skilled in the art that the polynucleotide sequence (or fragments thereof) of

```
ATGAGCCTCATCCGGAAAAAGGGCTTCTACAAGCAGGACGTCAACAAGACCGCCTGGGAG

CTGCCCAAGACCTACGTGTCCCCGACGCACGTCGGCAGCGGGGCCTATGGCTCCGTGTGC

TCGGCCATCGACAAGCGGTCAGGGGAGAAGGTGGCCATCAAGAAGCTGAGCCGACCCTTT

CAGTCCGAGATCTTCGCCAAGCGCGCCTACCGGGAGCTGCTGCTGCTGAAGCACATGCAG

CATGAGAACGTCATTGGGCTCCTGGATGTCTTCACCCCAGCCTCCTCCCTGCGCAACTTC

TATGACTTCTACCTGGTGATGCCCTTCATGCAGACGGATCTGCAGAAGATCATGGGGATG

GAGTTCAGTGAGGAGAAGATCCAGTACCTGGTGTATCAGATGCTCAAAGGCCTTAAGTAC

ATCCACTCTGCTGGGGTCGTGCACAGGGACCTGAAGCCAGGCAACCTGGCTGTGAATGAG

GACTGTGAACTGAAGATTCTGGATTTTGGGCTGGCGCGACATGCAGACGCCGAGATGACT

GGCTACGTGGTGACCCGCTGGTACCGAGCCCCCGAGGTGATCCTCAGCTGGATGCACTAC

AACCAGACAGTGGACATCTGGTCTGTGGGCTGTATCATGGCAGAGATGCTGACAGGGAAA

ACTCTGTTCAAGGGGAAAGATTACCTGGACCAGCTGACCCAGATCCTGAAAGTGACCGGG

GTGCCTGGCACGGAGTTTGTGCAGAAGCTGAACGACAAAGCGGCCAAATCCTACATCCAG

TCCCTGCCACAGACCCCCAGGAAGGATTTCACTCAGCTGTTCCCACGGGCCAGCCCCCAG

GCTGCGGACCTGCTGGAGAAGATGCTGGAGCTAGACGTGGACAAGCGCCTGACGGCCGCG

CAGGCCCTCACCCATCCCTTCTTTGAACCCTTCCGGGACCCTGAGGAAGAGACGGAGGCC

CAGCAGCCGTTTGATGATTCCTTAGAACACGAGAAACTCACAGTGGATGAATGGAAGCAG

CACATCTACAAGGAGATTGTGAACTTCAGCCCCATTGCCCGGAAGGACTCACGGCGCCGG

AGTGGCATGAAGCTG
``` or a variant, fragment, fusion or derivative thereof.

The invention also includes a polynucleotide comprising a fragment of the recombinant polynucleotide of the second aspect of the invention. Preferably, the polynucleotide comprises a fragment which is at least 10 nucleotides in length, more preferably at least 14 nucleotides in length and still more preferably at least 18 nucleotides in length. Such polynucleotides are useful as PCR primers.

The polynucleotide or recombinant polynucleotide may be DNA or RNA, preferably DNA. The polynucleotide may or may not contain introns in the coding sequence; preferably the polynucleotide is a cDNA.

A "variation" of the polynucleotide includes one which is (i) usable to produce a protein or a fragment thereof which is in turn usable to prepare antibodies which specifically the invention can be used to obtain other polynucleotide sequences that hybridise with it under conditions of high stringency. Such polynucleotides includes any genomic DNA. Accordingly, the polynucleotide of the invention includes polynucleotide that shows at least 55 per cent, preferably 60 per cent, and more preferably at least 70 per cent and most preferably at least 90 per cent homology with the polynucleotide identified in the method of the invention, provided that such homologous polynucleotide encodes a polypeptide which is usable in at least some of the methods described below or is otherwise useful.

Per cent homology can be determined by, for example, the GAP program of the University of Wisconsin Genetic Computer Group.

DNA-DNA, DNA-RNA and RNA-RNA hybridisation may be performed in aqueous solution containing between 0.1×SSC and 6×SSC and at temperatures of between 55° C. and 70° C. It is well known in the art that the higher the temperature or the lower the SSC concentration the more stringent the hybridisation conditions. By "high stringency" we mean 2×SSC and 65° C. 1×SSC is 0.15M NaCl/0.015M sodium citrate. Polynucleotides which hybridise at high stringency are included within the scope of the claimed invention.

"Variations" of the polynucleotide also include polynucleotide in which relatively short stretches (for example 20 to 50 nucleotides) have a high degree of homology (at least 80% and preferably at least 90 or 95%) with equivalent stretches of the polynucleotide of the invention even though the overall homology between the two polynucleotides may be much less. This is because important active or binding sites may be shared even when the general architecture of the protein is different.

A further aspect of the invention provides a replicable vector comprising a recombinant polynucleotide encoding a said protein kinase or a variant, fragment, derivative or fusion of said protein kinase or a fusion of said variant, fragment or derivative.

A variety of methods have been developed to operably link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'–5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487491. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued Apr. 3, 1984 to Rutter et al, U.S. Pat. No. 4,530,901 issued Jul. 23, 1985 to Weissman, U.S. Pat. No. 4,582,800 issued Apr. 15, 1986 to Crowl, U.S. Pat. No. 4,677,063 issued Jun. 30, 1987 to Mark et al, U.S. Pat. No. 4,678,751 issued Jul. 7, 1987 to Goeddel, U.S. Pat. No. 4,704,362 issued Nov. 3,1987 to Itakura et al, U.S. Pat. No. 4,710,463 issued Dec. 1, 1987 to Murray, U.S. Pat. No. 4,757,006 issued Jul. 12, 1988 to Toole, Jr. et al, U.S. Pat. No. 4,766,075 issued Aug. 23, 1988 to Goeddel et al and U.S. Pat. No. 4,810,648 issued Mar. 7, 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example Aspergillus), plant cells, anital cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells; such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (Ycps).

The present invention also relates to a host cell transformed with a polynucleotide vector construct of the present invention. The host cell can be either prokaryotic or eukaryotic. Bacterial cells are preferred prokaryotic host cells and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) Proc. Natl. Acad. Sci. USA 69, 2110 and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells.

For example, many bacterial species may be transformed by the methods described in Luchansky et al (1988) Mol. Microbiol. 2, 637–646 incorporated herein by reference. The greatest number of transformants is consistently recovered following electroporation of the DNA-cell mixture suspended in 2.5×PEB using 6250V per cm at 25 $\mu$FD.

Methods for transformation of yeast by electroporation are disclosed in Becker & Guarente (1990) Methods Enzymol. 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) J. Mol. Biol. 98, 503 or Berent et al (1985) Biotech. 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

A further aspect of the invention provides a method of making a stress-activated protein kinase or a variant, derivative, fragment or fusion thereof or a fusion of a variant, fragment or derivative the method comprising culturing a host cell comprising a recombinant polynucleotide or a replicable vector which encodes said stress-activated protein kinase, and isolating said protein kinase or a variant, derivative, fragment or fusion thereof of a fusion of a variant, fragment or derivative from said host cell. Methods of cultivating host cells and isolating recombinant proteins are well known in the art.

The invention also includes a stress-activated protein kinase, or a variant, fragment, derivative or fusion thereof, or fusion of a said variant or fragment or derivative obtainable by the above method of the invention.

A still further aspect of the invention provides an antibody reactive towards a stress-activated protein kinase of the invention.

Antibodies reactive towards the said stress-activated protein kinase of the invention may be made by methods well known in the art. In particular, the antibodies may be polyclonal or monoclonal.

Suitable monoclonal antibodies which are reactive towards the said protein kinase may be prepared by known techniques, for example those disclosed in "Monoclonal Antibodies: A mammal of techniques", H Zola (CRC Press, 1988) and in "Monoclonal Hybridoma Antibodies: Techniques and Applications", SGR Hurrell (CRC Press, 1982).

In a preferred embodiment the antibody is raised using any suitable peptide sequence obtainable from the given amino acid sequence of SAPK4. It is preferred if polyclonal antipeptide antibodies are made.

It is particularly preferred if the antibody does not react substantially with another stress-activated protein kinase such as SAPK2a, SAPK2b or SAPK3. Accordingly, it may be preferred if peptides based on the SAPK4 sequence are used which vary significantly from any peptides found in any other stress-activated protein kinases such as SAPK2a, SAPK2b or SAPK3.

Peptides in which one or more of the amino acid residues are chemically modified, before or after the peptide is synthesised, may be used providing that the function of the peptide, namely the production of specific antibodies in vivo, remains substantially unchanged. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism. The peptides may be present as single copies or as multiples, for example tandem repeats. Such tandem or multiple repeats may be sufficiently antigenic themselves to obviate the use of a carrier. It may be advantageous for the peptide to be formed as a loop, with the N-terminal and C-terminal ends joined together, or to add one or more Cys residues to an end to increase antigenicity and/or to allow disulphide bonds to be formed. If the peptide is covalently linked to a carrier, preferably a polypeptide, then the arrangement is preferably such that the peptide of the invention forms a loop.

According to current immunological theories, a carrier function should be present in any immunogenic formulation in order to stimulate, or enhance stimulation of, the immune system. It is thought that the best carriers embody (or, together with the antigen, create) a T-cell epitope. The peptides may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys, beta-galactosidase and the 163–171 peptide of interleukin-1. The latter compound may variously be regarded as a carrier or as an adjuvant or as both. Alternatively, several copies of the same or different peptides of the invention may be cross-linked to one another; in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4-(N-maleimidomethyl)cyclohexane-1-carboxylate, the latter agent exploiting the —SH group on the C-terminal cysteine residue (if present).

If the peptide is prepared by expression of a suitable nucleotide sequence in a suitable host, then it may be advantageous to express the peptide as a fusion product with a peptide sequence which acts as a carrier. Kabigen's "Ecosec" system is an example of such an arrangement. The peptide of the invention may be linked to other antigens to provide a dual effect.

Peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG72QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

A further aspect of the invention provides a method of identifying a compound that inhibits the activity of a stress-activated protein kinase as defined in the first aspect of the invention or of the stress-activated protein kinase SAPK3, the method comprising contacting a compound with the stress-activated protein kinase or a suitable variant, fragment, derivative or fusion thereof or a fusion of a variant, fragment or derivative thereof and determining whether the activity of the said is protein kinase is reduced compared to the activity of the said protein kinase or said variant, fragment, derivative or fusion thereof or a fusion of a variant, fragment or derivative thereof in the absence of said compound.

It will be appreciated that SAPK3 is a stress-activated protein kinase with a similar substrate specificity to SAPK4 (Cuenda et al (1997); Example 1 and Example 4). Conveniently, the method makes use of the fact that SAPK3 or SAPK4 phosphorylates myelin basic protein as described in Example 1 and Example 4, but any suitable substrate may be used. For example, Elk-1, ATF2, SAP-1, MAPKAP-K2, MAPKAP-K3, p53, SAP-2 or c-jun may be used as a substrate; Elk-1, ATF2 or SAP-1 are particularly preferred.

Conveniently, the method makes use of an assay which may be substantially the same as that disclosed in Example 4 and Cuenda et al (1997) *EMBO J.* 16, 295–305, incorporated herein by reference, except that SAPK3 may be replaced by SAPK4.

A still further aspect of the invention provides a method of identifying a compound which blocks the activation of the said stress-activated protein kinase as defined in the first aspect of the invention or the stress-activated protein kinase SAPK3 by SKK3 the method comprising determining whether a compound enhances or disrupts the interaction between (a) a stress-activated protein kinase as defined in the first aspect of the invention or SAPK3 or a suitable fragment, variant, derivative or fusion thereof or a suitable fusion of a fragment, variant or derivative and (b) SKK3 or a suitable variant, derivative, fragment or fusion thereof or a suitable fusion of a variant, derivative or fragment, or determining whether the compound substantially blocks activation of the said stress-activated protein kinase or a suitable variant, fragment, derivative or fusion thereof, or a fusion of a said fragment, derivative or fusion by SKK3 or a suitable variant, derivative, fragment or fusion thereof.

Activation of SAPK3 or SAPK4 by SKK3 or SKK1 may be assayed substantially as described in Example 4 or Cuenda et al (1997) *EMBO J.* 16, 295–305, incorporated herein by reference, except that SAPK3 may be replaced by SAPK4.

By "SKK3" we mean stress-activated protein kinase kinase 3 (SAP kinase kinase 3; SAPKK3) as described in Example 1. SKK1 may also be used and so the invention also includes a method of identifying a compound which blocks the activation of the said stress-activated protein as defined in the first aspect of the invention by SKK1.

Conveniently, the said stress-activated protein kinase or fragment, derivative, variant or fusion thereof used in the method is one which is produced by recombinant DNA technology. Similarly, it is preferred if the SKK3 or fragment, derivative, variant or fusion thereof used in the method is one which is produced by recombinant DNA technology.

It is also preferred if SKK3 is SKK3 purified from an appropriate natural source; for example, SKK3 may be purified using the method described in Cuenda et al (1996) *EMBO J.* 15, 4156–4164.

It will be appreciated that by "suitable" we mean that the said components in the method are those that have interactions or activities which are substantially the same as those of SAPK3 or SAPK4 or SKK3 as the case may be but which may be more convenient to use in an assay. For example, fusions of SAPK3 or SAPK4 or SKK3 are particularly useful since fusion may contain a moiety which may allow the fusion to be purified readily.

The enhancement or disruption of the interaction between the said stress-activated protein kinase and SKK3, or suitable derivatives, fragments, fusions or variants can be measured in vitro using methods well known in the art of biochemistry and include any methods which can be used to assess protein-protein interactions.

The said interaction can also be measured within a cell, for example using the yeast two hybrid system as is well known in the art.

It will be appreciated that the invention provides screening assays for drugs which may be useful in modulating the activity of SAPK3 or SAPK4 or their interactions with SKK3. The compounds identified in the methods may themselves be useful as a drug or they may represent lead compounds for the design and synthesis of more efficacious compounds.

A further aspect of the invention provides a compound identifiable by the screening methods of the invention. A still further aspect provides such a compound for use in medicine.

It is believed that such compounds are useful in treating inflammatory disease. Inflammatory diseases include rheumatoid arthritis, psoriasis, septic shock, asthma and inflammatory bowel disease.

Thus, a further aspect of the invention provides a method of treating a patient with an inflammatory disease the method comprising administering to the patient an effective amount of a compound identifiable by the screening methods of the invention.

A still further invention provides a use of a compound identifiable by the screening methods of the invention in the manufacture of a medicament for treating an inflammatory disease in a patient.

The aforementioned compounds of the invention or a formulation thereof may be administered by any conventional method including oral and parenteral (e.g. subcutaneous or intramuscular) injection. The treatment may consist of a single dose or a plurality of doses over a period of time.

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen free. Thus, the invention also provides pharmaceutical compositions comprising the compound identifiable by the screening methods of the invention and a pharmaceutically acceptable carrier.

Further aspects of the invention provide a use of a stress-activated protein kinase or a variant, fragment, derivative or fusion thereof or a fusion of a said variant, derivative or fragment as defined in the first aspect of the invention in a screening assay for compounds which inhibit the activity of the said protein kinase or which block the activation of said protein kinase by SKK3.

A further aspect of the invention provides a kit of parts that are useful in carrying out the screening methods.

A still further aspect of the invention provides the use of SAPK3 (in vitro or in vivo), its analogues, isoforms, inhibitors, activators and the functional equivalents thereof in the regulation of protein phosphorylation, gene expression and/or protein synthesis. A composition comprising such agents is also covered by the present invention, and the use of such a composition for treatment of disease states where protein phosphorylation, gene expression and/or protein synthesis exhibit abnormality is also provided.

The invention also provides the use of SAPK3 in the manufacture of a medicament for the treatment of disease states where protein phosphorylation, gene expression and/ or protein synthesis exhibit abnormality.

Also provided is a method (in vitro or in vivo) of identifying agents able to influence the activity of SAPK3, said method comprising:

a. exposing a test substance to SAPK3 or a functional equivalent thereof in the presence of a substrate for SAPK3;

b. detecting whether (and, optionally, to what extent) said substrate has been phosphorylated.

Detection of the presence and/or amount of phosphate associated with or dissociated from the substrate after the assay may be conducted by any convenient means. Generally detection may be accomplished by using labelled (e.g. radiolabelled) phosphate in free solution or attached to the substrate, and comparing the amount associated with (or dissociated from) the substrate before and after the assay.

The test substance may be an analogue, isoform, inhibitor, or activator of SAPK3.

The substrate can comprise myelin basic protein (MBP), or a transcription factor such as ATF-2. In certain embodiments the test substance can itself act as a substrate, and can be capable of being phosphorylated. Thus, the substrate can be a phosphatase which is itself capable of affecting protein phosphorylation, gene expression and/or protein synthesis.

Some of the assay components may be localised on a surface, such as a blotting membrane, or an assay plate for ELISA etc, although the assay can be carried out in solution.

A further aspect of the invention is the use of SKK3 in a method of identifying agents able to influence the activity of a stress-activated protein kinase or a variant, fragment, derivative or fusion thereof or a fusion of a said variant, derivative or fragment as defined in the first aspect of the invention (SAPK4) or SAPK3 or a variant, fragment, derivative or fusion thereof or a fusion of a said variant, derivative or fragment thereof (SAPK3), said method comprising:

a) exposing SAPK4 or SAPK3 to SKK3;
b) exposing a test substance to SAPK4 or SAPK3 in the presence of a substrate for SAPK4 or SAPK3 respectively;
c) detecting whether (and, optionally, to what extent) said substrate has been phosphorylated.

A still further aspect is a method of activating a stress-activated protein kinase or a variant, fragment, derivative or fusion thereof or a fusion of a said variant, derivative or fragment as defined in Claim 1 (SAPK4) or SAPK3 or a variant, fragment, derivative or fusion thereof or a fusion of s a said variant, derivative or fragment thereof (SAPK3), said method comprising incububating SAPK4 or SAPK3 with SKK3.

It will be appreciated that SKK1 and SKK3 may be functional equivalents with regard to activating SAPK3 and SAPK4, and that SKK1 may be used instead of SKK3. It is preferred that SKK3 is used.

It will be appreciated that the SKK3 or SKK1 may be purified; preferably the SKK3 or SKK1 is purified. It will further be appreciated that the SKK3 or SKK1 may be recombinant.

In a further aspect the present invention provides a method of treatment of the human or non-human (preferably mammalian) animal body, said method comprising administering SAPK3, its analogues, inhibitors, stimulators or functional equivalents thereof to said body. Said method affects the regulation of gene expression in the treated body, preferably by affecting the activity of gene transcription factors.

The present invention also provides a therapeutic agent able to affect gene expression and cell regulation by interaction with SAPK3, its analogues, inhibitors, stimulators or functional equivalents. Such therapeutic agents are likely to be efficacious as anti-inflammatory agents, and/or as immunosuppressants, anti-apoptosis and anti-cancer drugs.

Variants (whether naturally-occurring or otherwise) may be made using the methods of protein engineering and site-directed mutagenesis well known in the art using the recombinant polynucleotides described below. By "fragment of said protein kinase" we include any fragment which retains activity or which is useful in some other way, for example, for use in raising antibodies or in a binding assay.

By "fusion of said protein kinase" we include said protein kinase fused to any other polypeptide. For example, the said protein kinase may be fused to a polypeptide such as glutathione-S-transferase (GST) or protein A in order to facilitate purification of said protein kinase. Similarly, the said protein kinase may be fused to an oligo-histidine tag such as $His_6$ or to an epitope recognised by an antibody such as the well known Myc tag epitope. Fusions to any variant, fragment or derivative of said protein kinase are also included in the scope of the invention.

The present invention will now be described in more detail with reference to the following, non-limiting, Figures and Examples in which:

FIG. 1 shows the nucleotide sequences identified as SEQ. ID. NO: 3 (nucleotides 1–1259) and SEQ. ID. NO: 2 (nucleotides 23–1117) and predicted amino acid sequence identified as SEQ. ID. NO: 1 of human SAP kinase-4. Nucleotides are numbered in the 5' to 3' direction and amino acids are shown in single-letter code above the nucleotide sequence. The in-frame termination codon is marked by an asterisk.

FIG. 2 shows the sequence comparison of human SAPK4 (SEQ. ID. NO: 1), human SAPK3 (Goedert et al, 1997)(also called ERK6 and p38γ), human SAPK2a (Lee et al, 1994) (also called p38, p40, RK, CSBP2, Mxi2 and XMpk2), human SAPK2b (also called p38β) and HOG1 from *S. cerevisiae* (Brewster et al, 1993). Amino acids were aligned and gaps were introduced to maximise the homology. Amino acid identities between at least three of the five sequences are indicated by black bars. Asterisks denote the dual phosphorylation sites in the TGY motif of the activation domain. The SAPK2b sequence shown here differs from the published p38β sequence (Jiang et al, 1996)(see Discussion in Example 1). The amino acid sequence of SAPK3 (Goedert et al, 1997) differs in 13 positions from the ERK6 sequence of Lechner et al, (1996) and in 1 amino acid from the p38γ sequence of Li et al (1996).

FIG. 3 shows an RNA blot analysis of poly(A)+ RNA from adult human tissues, with [$^{32}$P]-labelled SAPK4 DNA as the probe. Size markers (in kb) are marked to the left. Lanes: 1, heart; 2, brain; 3, placenta; 4, lung; 5, liver; 6, skeletal muscle; 7, kidney; 8, pancreas; 9, spleen; 10, thymus; 11, prostate gland; 12, testis; 13, ovary; 14, small intestine; 15, colon; 16, leucocytes.

Figure 4:
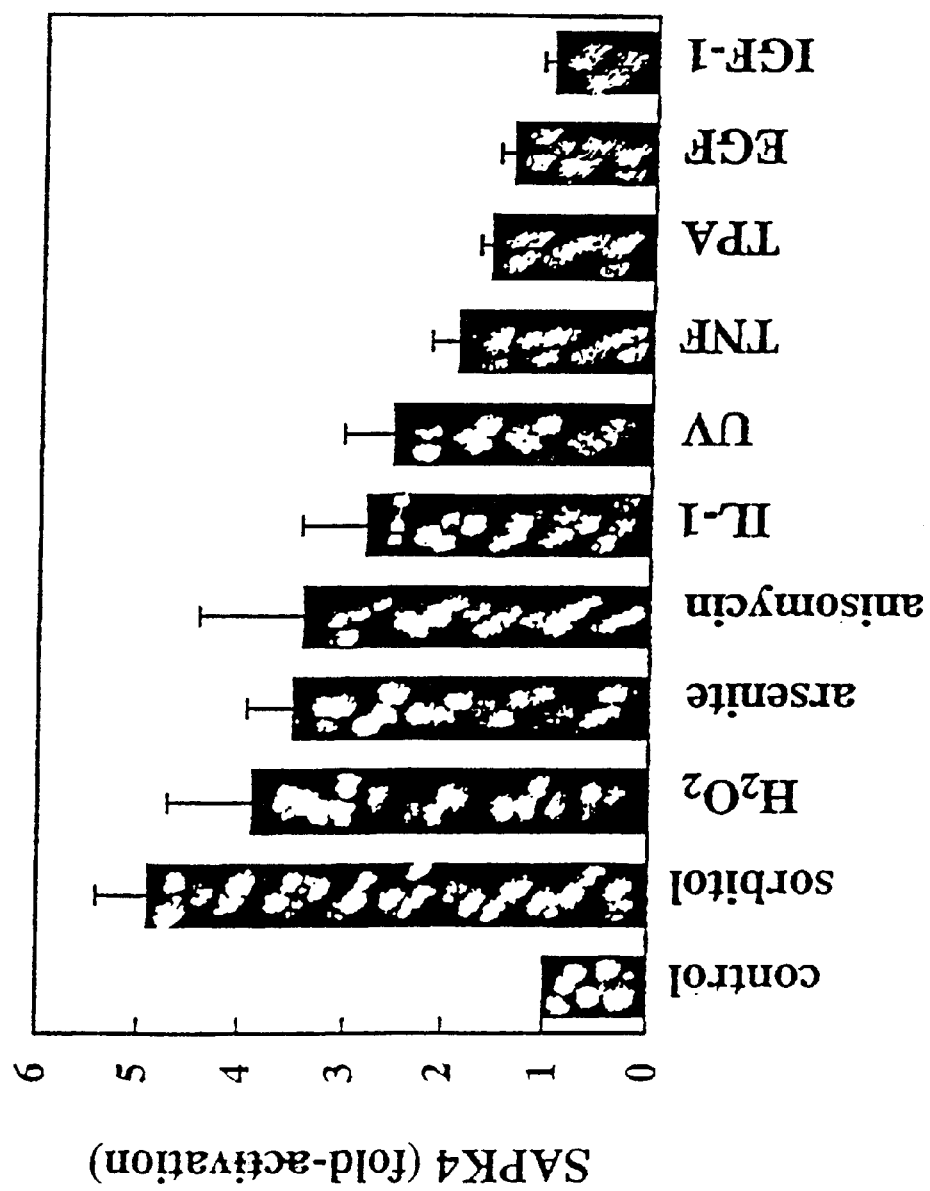

FIG. 4 shows that SAPK4 is activated by cytokines and cellular stresses in KB and 293 cells. KB cells were transiently transfected with a DNA construct encoding myc epitope-tagged SAPK4, as indicated in Methods. Cells were stimulated in DMEM for 15 min with 0.5 M sorbitol, 1 mM $H_2O_2$, 20 ng/ml IL1alpha, 0.5 mM sodium arsenite, 100 ng/ml TNFalpha, 100 ng/ml EGF or 300 ng/ml TPA; for 30 min with 10 μg/ml anisomycin or for 10 min with 100 ng/ml IGF-1. UV irradiation was at 60 J/m$^2$ and the cells were lysed 30 min later. Following stimulation, the myc epitope-tagged SAPK4 was immunoprecipitated from cell lysates using monoclonal antibody 9E10 and the kinase activity measured using MBP as the substrate, as indicated in Materials and Methods in Example 1. The results are shown as the average±SEM of four experiments.

Figure 5:
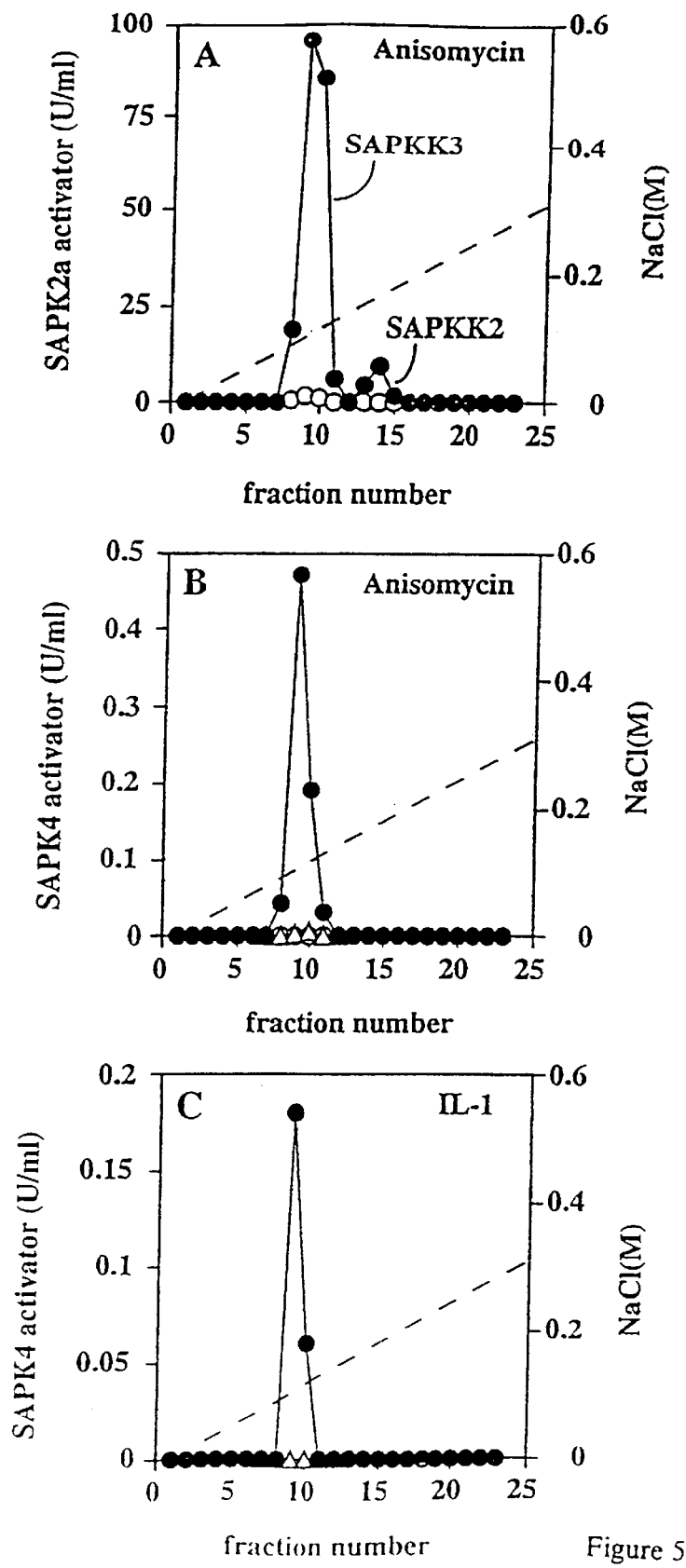

FIG. 5 shows that SKK3 is the major SAPK4 activator in KB cells. Cell lysates (0.6 mg protein) from quiescent KB cells (open circles in A) or cells stimulated for 30 min with 10 μg/ml anisomycin (closed circles in A and B) or for 15 min with 20 ng/ml IL1alpha (closed circles in C) were chromatographed on Mono S, and activators of SAPK2a (A) or activation of SAPK4 (B and C) assayed as described in Methods. Aliquots from the peak of SAPK4 activator seen in (B) and (C) were immunoprecipitated, as described previously (Cuenda et al, 1996) using anti-MKK6 antibodies and the SAPK4 activator remaining in the supernatant was assayed (open triangles in B and C). Similar results were obtained in three different experiments.

FIG. 6 shows the phosphorylation and activation of SAPK4 and SAPK2a by purified SKK3. (A) GST-SAPK4 (0.5 μM, open circles) or MalE-Mpk2, the Xenopus homologue of SAPK2a (0.5 μM, closed circles), were phosphorylated using 100 U/ml SKK3 and unlabelled ATP and SAPK activities were measured at the times indicated using MBP as substrate. (B) GST-SAPK4, an inactive mutant GST-SAPK4(D168A) and MalE-Mpk2 were phosphorylated for 2 h as in (A), but using [$^{32}$P]ATP (Cuenda et al, 1997). Aliquots of the reactions were precipitated by the addition of 1 ml of 20% (by mass) TCA, the suspension centrifuged for 5 min at 13000×g and the pellets washed three times with 20% (by mass) TCA, five times with water and dried.

The samples were then incubated for 90 min at 110° C. in 6 M HCl, electrophoresed on thin layer cellulose at pH 3.5 to resolve phosphoserine (pS), phosphothreonine (pT) and phosphotyrosine (pY), and autoradiographed.

Figure 7:
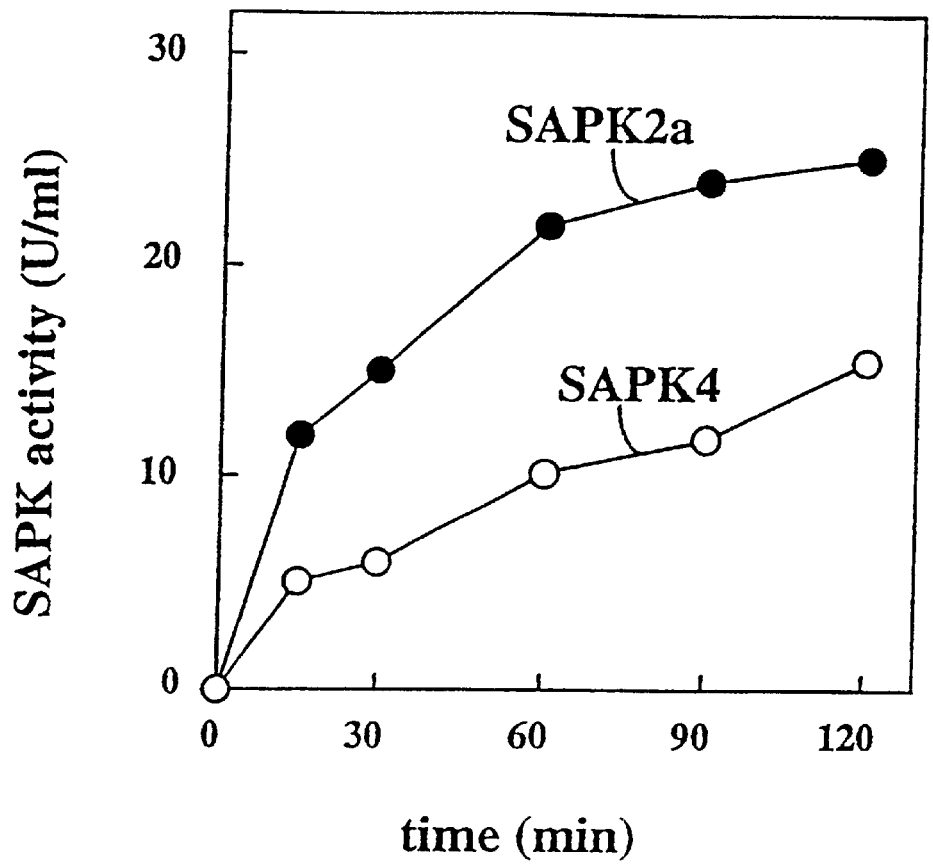

FIG. 7 shows the activation of SAPK4 and SAPK2a by SKK1 (MKK4). GST-SAPK4 (0.5 μM, open circles) or MalE-Mpk2, the Xenopus homologue of SAPK2a (0.5 μM, closed circles) were incubated with 100 U/ml SKK1 and unlabelled ATP and the generation of SAPK activity measured at the times indicated using MBP as substrate.

Figure 8:
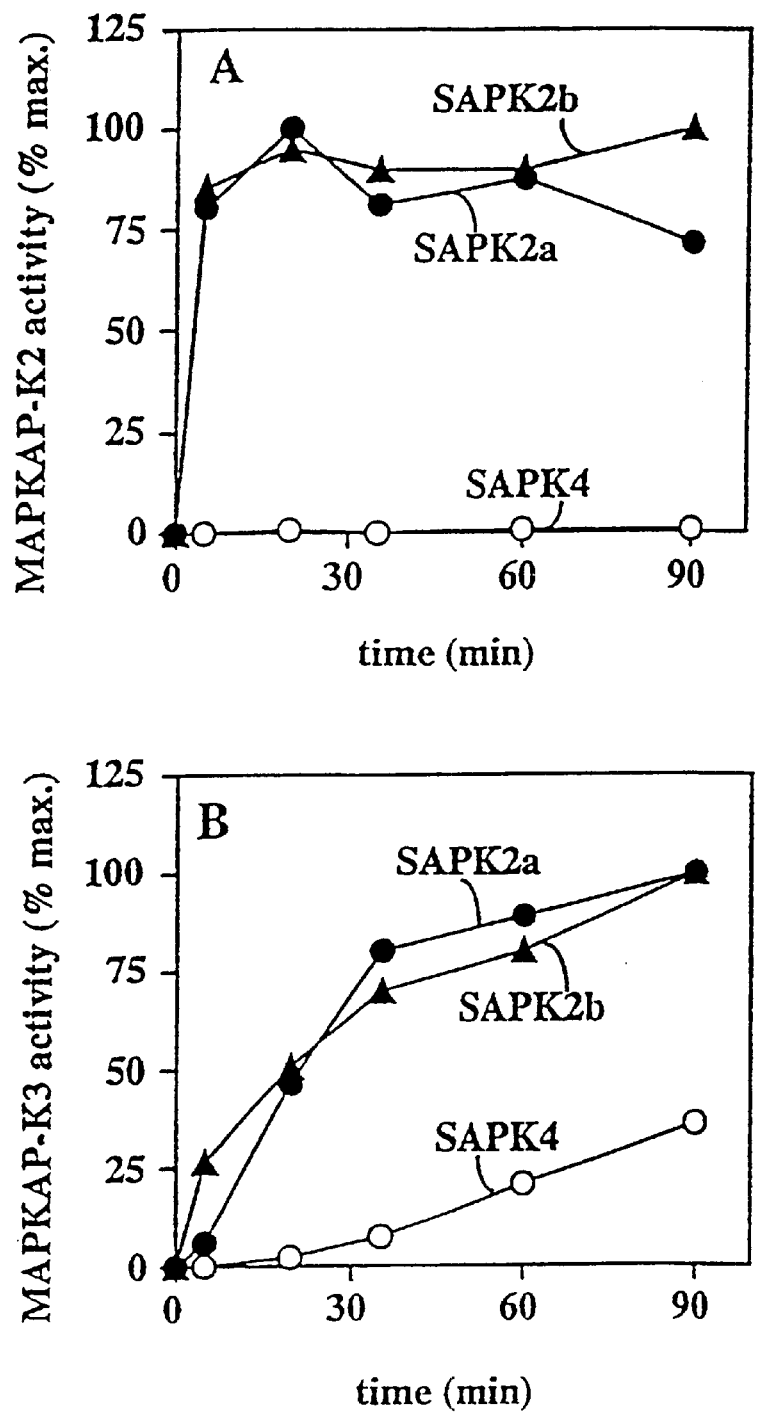

FIG. 8 shows the activation of MAPKAP-K2 and MAPKAP-K3 by SAPK2a, SAPK2b and SAPK4. (A) GST-MAPKAP-K2(5400) or (B) GST-MAPKAP-K3 (0.2 mg/ml) were incubated with unlabelled ATP and 5 U/ml of the Xenopus homologue of SAPK2a (closed circles), 5 U/ml of SAPK2b (closed triangles) or 5 U/ml of SAPK4 (open circles) and MAPKAP-K2/K3 activity measured at the times indicated, as described in Methods. There was no phosphorylation or activation of GST-MAPKAP-K2(5-400) or GST-MAPKAP-K3 when SAPK2a, SAPK2b or SAPK4 were omitted.

Figure 9:
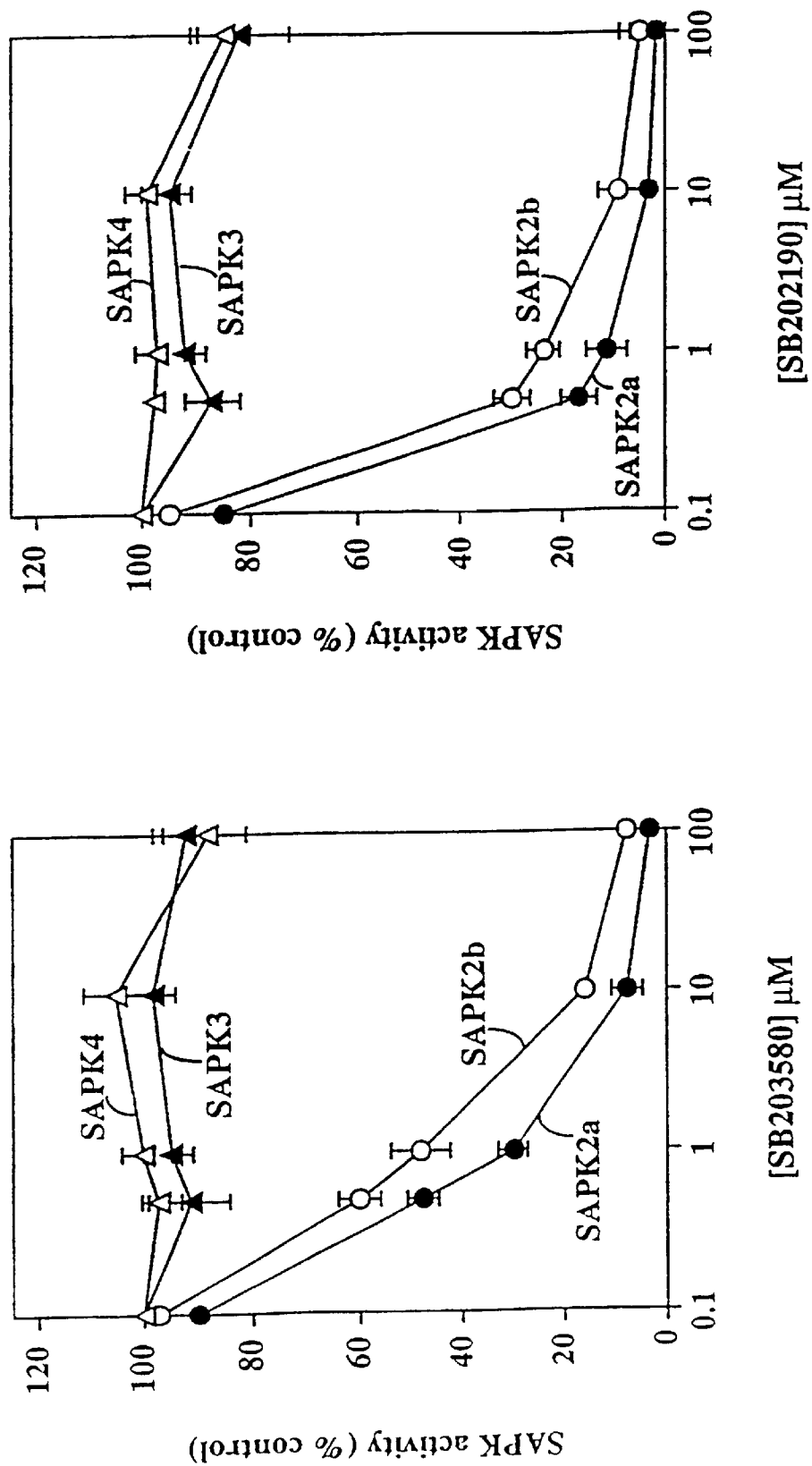

FIG. 9 shows the effects of SB 203580 or SB 202190 on SAPK2a, SAPK2b, SAPK3 and SAPK4. The Xenopus homologue of SAPK2a (closed circles), human SAPK2b (open circles), human SAPK3 (closed triangles) and human SAPK4 (open triangles) were activated in vitro with purified SKK3, as in FIG. 7, and then assayed after a 10 min incubation with the indicated concentrations of SB 203580 or SB 202190. The results are presented relative to control incubations in which the inhibitor was omitted.

Figure 10:
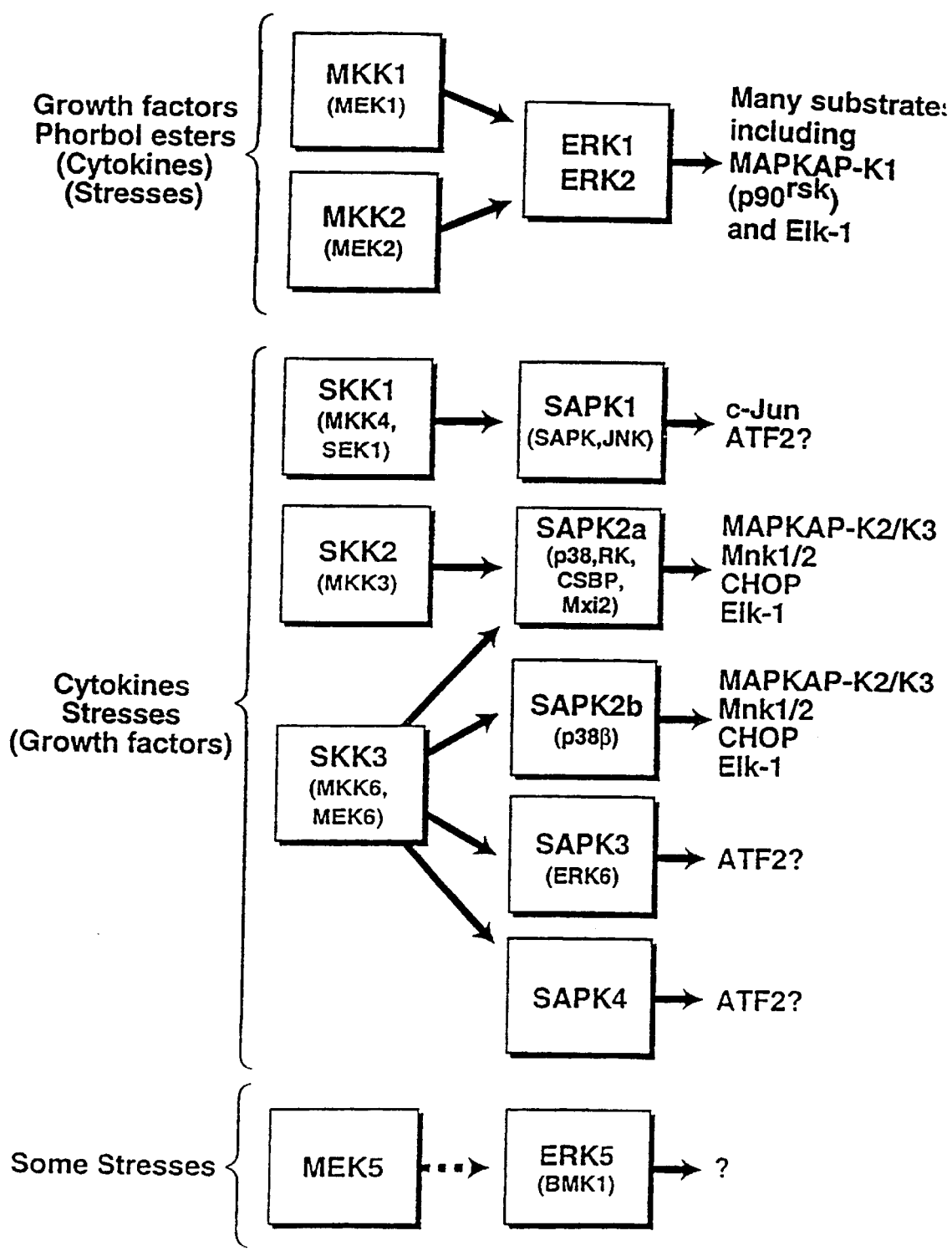

FIG. 10 shows a schematic representation of mammalian MAP kinase and SAP kinase signal trasduction pathways. Following growth factor or phorbol ester stimulation, the MAP kinase kinases MKK1 and MKK2 (also called MEK1 and MEK2) activate the ERK1 and ERK2 group of MAP kinases. ERK1 and ERK2 (also termed p44 and p42 MAP kinases, respectively) phosphorylate a number of substrates, including the protein kinase MAPKAP-K1 (also called p90$^{rsk}$) and the transcription factor Elk-1. In some cellular backgrounds, pro-inflammatory cytokines and cellular stresses also activate the MAP kinase pathway, albeit more weakly than growth factors or phorbol esters (indicated by brackets). SAP kinase (SAPK) pathways are strongly activated by pro-inflammatory cytokines and a large number of stressful stimuli. In some cells they are also activated more weakly by certain growth factors (indicated by brackets). The SAP kinase kinase SKK1 (also termed MKK4 and SEK1) activates SAPK1 (also called SAPK or JNK) which phosphorylates the transcription factor c-Jun. The highly homologous SAPK1 isoforms are the products of three different genes. The SAP kinase kinase SKK2 (also called MKK3) activates SAPK2a (also termed p38, RK, CSBP and Mxi2). The SAP kinase kinase SKK3 (also called MKK6 or MEK6) activates SAPK2a, SAPK2b (also termed p38β), SAPK3 (also called ERK6 and p38γ) and SAPK4. Additional forms of SAPK1, SAPK2a and SAPK3 are produced by alternative mRNA splicing. Studies with the specific inhibitor SB 203580 indicate that SAPK2a (and probably SAPK2b) phosphorylate the protein kinases MAPKAP-K2/3 and Mnk1/2, as well as the transcription factors CHOP and Elk-1. The reason why ATF2 is an unlikely physiological substrate for SAPK2a and SAPK2b is given in the text, and this transcription factor may therefore be phosphorylated by SAPK1, SAPK3 and/or SAPK4 in vivo. SKK1 activates SAPK2a and SAPK2b in vitro and in transfection experiments, but is not thought to activate these enzymes in vivo. SKK1 also activates SAPK3 and SAPK4 weakly in vitro, but not in transfection experiments. Oxidative and osmotic stresses activate ERK5 (also called BMK1) which is believed to be activated by MEK5, although this has not been shown directly (indicated by broken arrow). Question marks indicate that a given SAPK phosphorylates a target protein in vitro, with no current evidence for a corresponding role in vivo. Although SAPK1 phosphorylates Elk-1 in vitro, it is not rate-limiting for the phosphorylation of this protein in vivo, since the phosphorylation of Elk-1 and the transcription of c-fos are completely suppressed by SB 203580 and PD 098059 (Hazzalin et al, 1996; Price et al, 1996). PD 098059, a specific inhibitor of the activation of MKK1 (Alessi et al, 1995a), prevents activation of ERK1 and ERK2.

FIG. 11. SAPK3 is activated by cytokines and cellular stresses in KB and 293 cells. KB cells (A) or 293 cells (B) were transiently transfected with a DNA construct expressing a myc epitope-tagged SAPK3. Cells in DMEM were stimulated for 15 min with 0.5 M sorbitol (an osmotic shock), 20 ng/ml IL-1α, 100 ng/ml TNFa, 0.5 mM sodium arsenite (a chemical stress), 100 ng/ml of EGF or 300 ng/ml TPA, or for 30 min with 10 mg/ml anisomycin or 10 min with 100 ng/ml IGF-1. UV-C irradiation of cells was carried out at 60 J/m2 (KB cells) or 200 J/m2 (293 cells) and the cells then left for a further 30 min at 37° C. before lysis. The myc epitope-tagged SAPK3 was immunoprecipitated from cell lysates using the 9E10 monoclonal antibody and assayed with MBP as substrate. The figure shows the fold-activation of SAPK3 in response to each stimulus and the results are presented as ±SEM for three experiments. After UV-C irradiation, SAPK3 activity in the extracts was 0.18 U/mg (KB cells) and 0.1 U/mg (293 cells). Immunoblotting experiments showed that SAPK3 was expressed at a similar level in each experiment.

FIG. 12. SKK3 is the major SAPK3 activator in 293 cells. Cell lysates (0.8 mg of protein) from unstimulated 293 cells (open circles) or cells shocked osmotically for 15 min with 0.5 M sorbitol (closed circles) were chromatographed on Mono S (5×0.16 cm) using a Pharmacia Smart System (Cuenda et al, 1995). The fractions were assayed for activators of SAPK2 (A) or SAPK3 (C) as described under Methods. The broken line shows the NaCl gradient. Similar results were obtained in three different experiments. The two major SAPK2 activators from A (I and II) were pooled separately and immunoprecipitated using anti-MKK6 antibodies, anti-MKK4 antibodies or anti-MKK3 antibodies. Panel B shows the amount of SAPK2 activator remaining in the supernatant and panel D the amount of SAPK3 activator remaining in the supernatant after immunoprecipitation in the presence (+) or absence (−) of the appropriate competing peptide immunogen (0.6 mM), relative to control incubations (100%) where antibody was omitted. The results presented are the average±SEM for three separate experiments.

Figure 13:
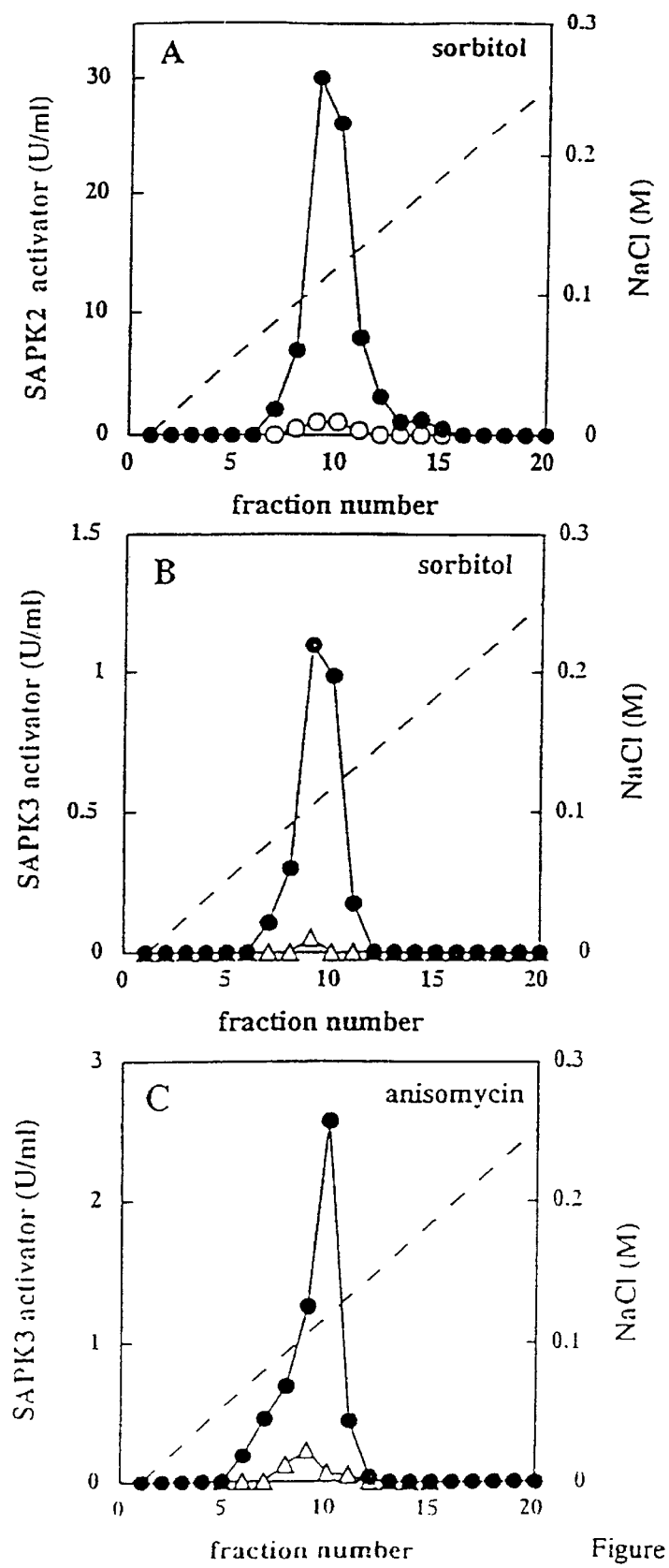

FIG. 13. SKK3 is the major activator of SAPK3 in KB cells. A and B; cell lysates (0.4 mg of protein) from unstimulated KB cells (open circles) or cells stimulated with 0.5 M sorbitol (closed circles) were chromatographed on Mono S, and the fractions assayed for activators of SAPK2 (A) or for activators of SAPK3 (B). Aliquots of each fraction were immunoprecipitated using anti-MKK6 antibodies and the supernatants reassayed for activators of SAPK3 (open triangles). No SAPK3 activator was detected in unstimulated cells (see FIG. 1A). The broken lines show the NaCl gradient. Similar results were obtained in three different experiments (C) Cells were stimulated for 30 min with 10 μg/ml anisomycin instead of sorbitol and assayed for SAPK3 activators before (closed circles) and after (open triangles) immunoprecipitation of SKK3.

Figure 14:
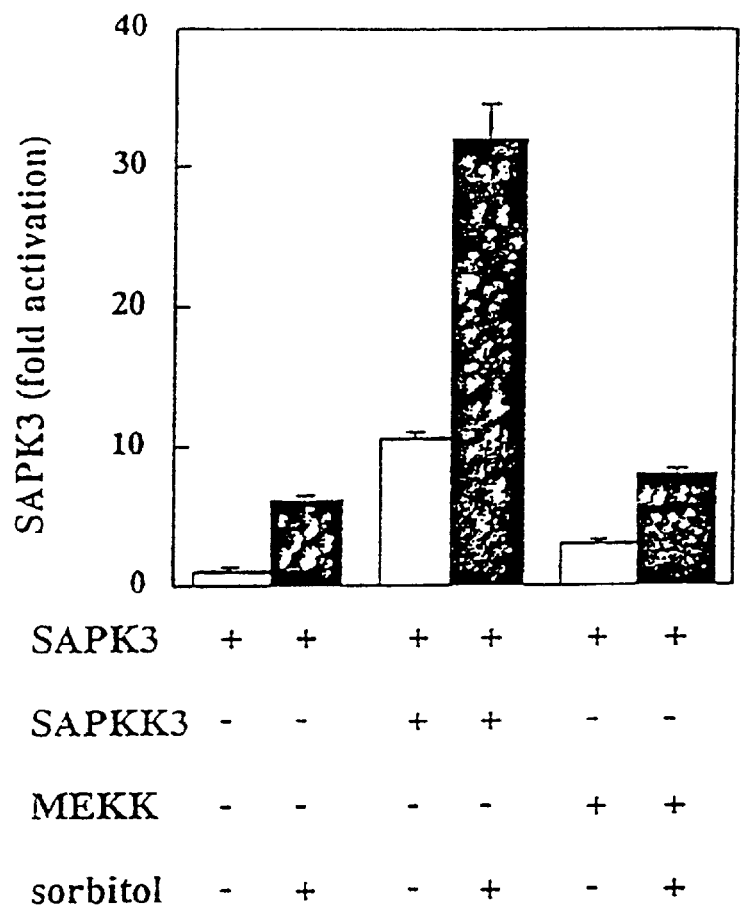

FIG. 14. SKK3 activates SAPK3 in transfected cells. COS-1 cells were transiently transfected with DNA expressing SAPK3 or co-transfected with either SKK3 or MEK kinase (MEKK). Cells were stimulated in DMEM for 15 min or with 0.5 M sorbitol. After stimulation and lysis, SAPK3 was immunoprecipitated from the cell lysates using an anti-SAPK3 antibody raised against the C-terminal 16 residues of SAPK3 (see Methods) and activity measured using MBP as the substrate. The figure shows the fold-activation of SAPK3 in response to sorbitol and/or cotransfection with SKK3 relative to unstimulated cells transfected with SAPK3 alone.

FIG. 15. Phosphorylation and activation of SAPK3 and SAPK2 by purified SKK3. (A) GST-SAPK3 (0.5 μM) and (B) the Xenopus homologue of SAPK2 (MalE-Mpk2, 0.5 μM) were incubated with unlabelled MgATP and 100 U/ml SKK3 and the generation of activity (closed circles) measured at the times indicated using MBP as substrate. No activation of either GST-SAPK3 or MalE-Mpk2 occurred when SKK3 was first inactivated with PP2A (open circles). Phosphorylation of GST-SAPK3 or MalE-Mpk2 (open triangles) was determined in parallel incubations using [γ-$^{32}$P]ATP ($10^6$ cpm per nmol) and in (C) the 15 and 120 min time points from A and B were partially hydrolysed for 90 min in 6 M HCl at 110° C., electrophoresed on thin layer cellulose at pH 3.5 and autoradiographed to identify phosphoserine (pS), phosphothreonine (pT) and phosphotyrosine (pY). (D) same as the 120 min time point in C, except that wild-type SAPK3 was replaced by a kinase-inactive mutant in which Asp-171 was changed to Ala.

Figure 16:
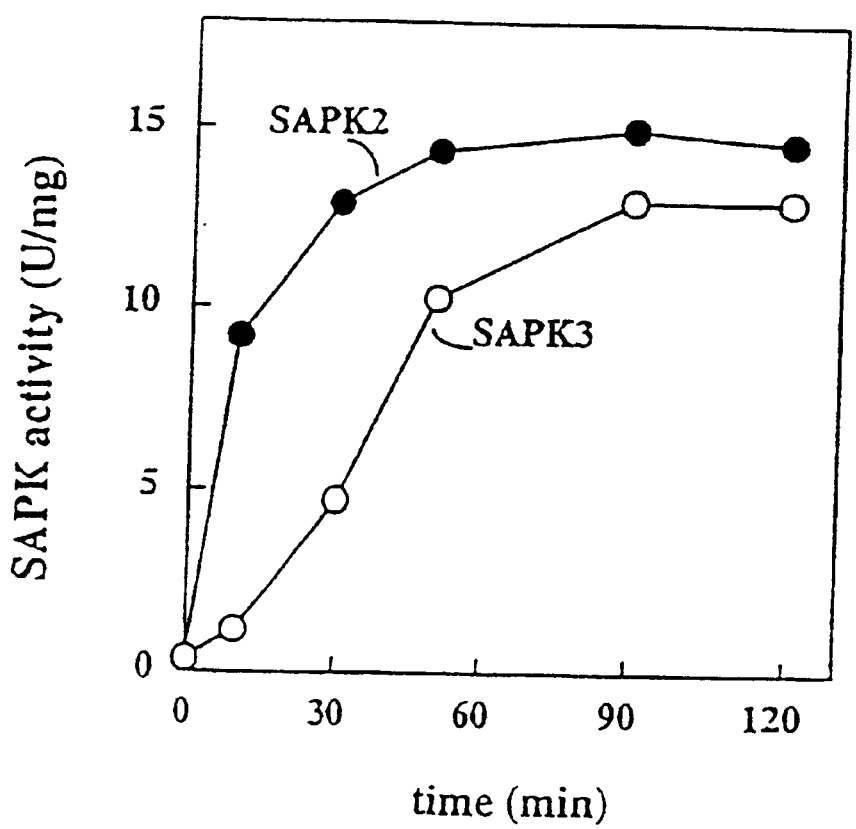

FIG. 16. Activation of SAPK3 and SAPK2 by SKK1 (MKK4). GST-SAPK3 (0.5 mM, open circles) or a MalE fusion protein of the Xenopus homologue of SAPK2 (0.5 μM, closed circles) was incubated with unlabelled MgATP and 100 U/ml SKK1 and the generation of activity measured at the times indicated using MBP as substrate.

Figure 17:
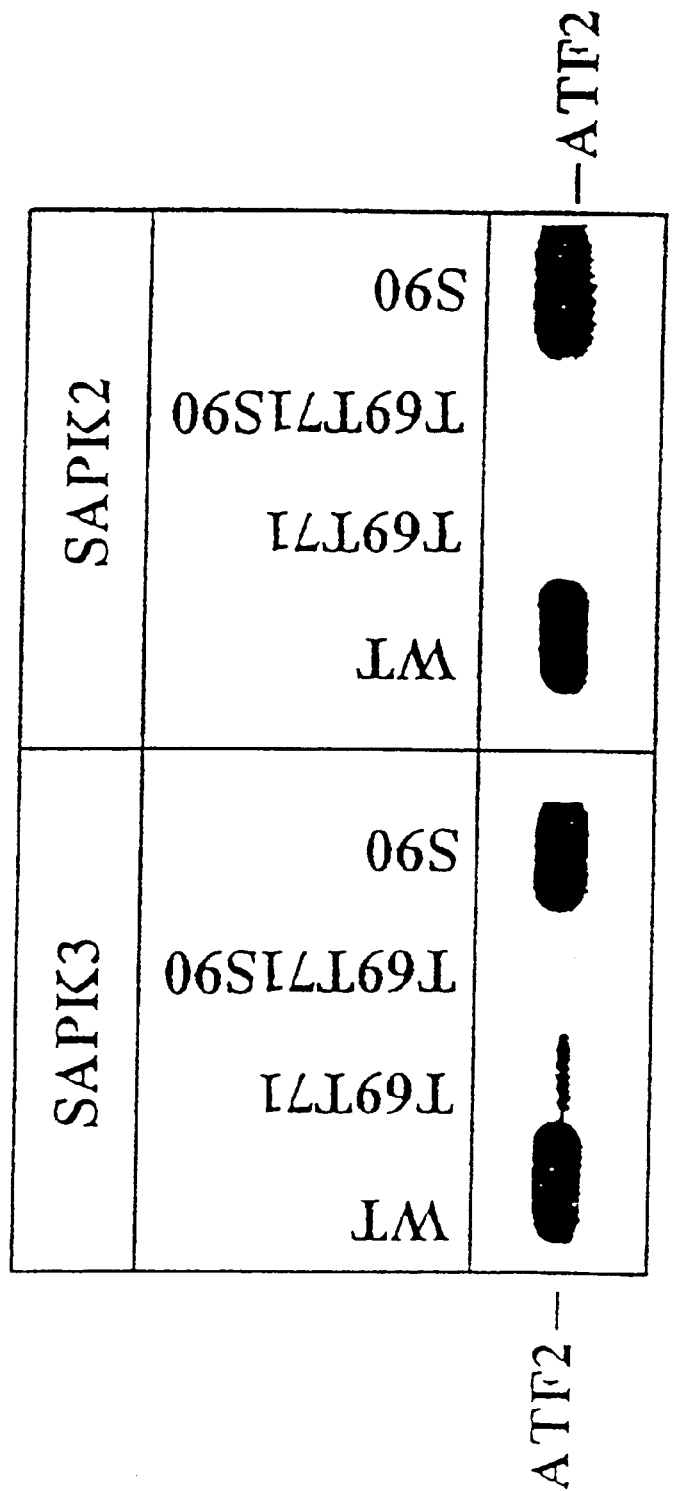

FIG. 17. Identification of the sites on ATF2 phosphorylated by SAPK3 and SAPK2. GST-SAPK3 and the Xenopus homologue of SAPK2 were matched for activity against MBP and each enzyme (0.4 U/ml) incubated for 30 min at 30° C. with 1 mM wild type (WT) or mutant GST-ATF2 (19–96) and Mg[γ-$^{32}$P]ATP in a total volume of 50 ml. The reactions were stopped by adding 5 ml of 6% (by mass) SDS and the samples electrophoresed on 10% SDS/polyacrylamide gels and autoradiographed. Abbreviations:- T69T71, mutant in which Thr-69 and Thr-71 were mutated to Ala; T69T71S90, mutant in which Thr-69, Thr-71 and Ser-90 were mutated to Ala; S90, mutant in which Ser-90 was mutated to Ala.

FIG. 18. Activation of MAPKAP-K2 and MAPKAP-K3 by SAPK2 and SAPK3. (A) GST-MAPKAP-K2 (46–400), (B) GST-MAPKAP-K3 or (C) GST-MAPKAP-K2 (5–400) (0.2 mg/ml), were incubated with unlabelled MgATP and 0.3 U/ml SAPK2 (closed circles) or 0.3 U/ml SAPK3 (open circles) and activation measured at the times indicated. There was no phosphorylation or activation of MAPKAP-K2 or GST-MAPKAP-K3 when SAPK2 and SAPK3 were omitted.

Figure 19:
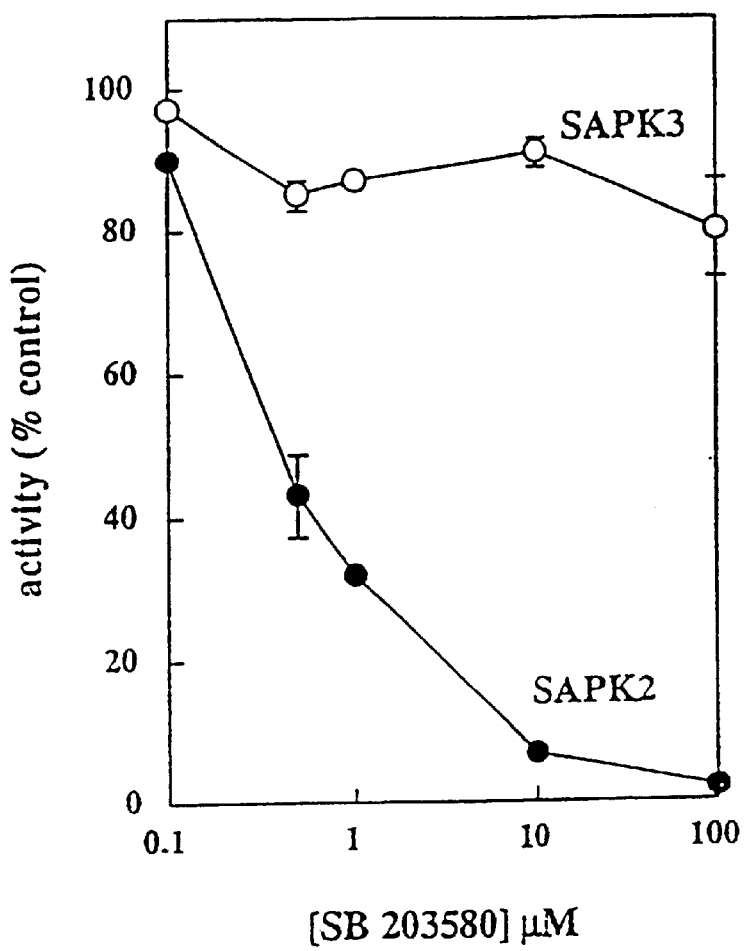

FIG. 19. Effect of SB 203580 on the activity of SAPK3 and SAPK2. SAPK3 (open circles) and SAPK2 (closed circles) were activated in vitro with purified SKK3 (FIG. 5) and then assayed in the presence the indicated concentrations of SB 203580. The results are presented relative to the control incubations in which the inhibitor was omitted.

EXAMPLE 1

Activation of the Novel Stress-activated Protein Kinase SAPK4 by Cytokines and Cellular Stresses is Mediated by SKK3 (MKK6); Comparison of its Substrate Specificity With That of Other SAP Kinases Summary A cDNA was cloned that encodes human stress-activated protein kinase-4 (SAPK4), a novel MAP kinase family member whose amino acid sequence is approximately 60% identical to that of the other three SAP kinases which contain a TGY motif in their activation domain. The mRNA encoding SAPK4 was found to be widely distributed in human tissues. When expressed in KB cells, SAPK4 was activated in response to cellular stresses and pro-inflammatory cytokines, in a manner similar to other SAPKs. SAPK4 was activated in vitro by SKK3 (also called MKK6) or when co-transfected with SKK3 into COS cells. SKK3 was the only activator of SAPK4 which was induced when KB cells were exposed to a cellular stress or stimulated with interleukin-1. These findings indicate that SKK3 mediates the activation of SAPK4. The substrate specificity of SAPK4 in Vitro was similar to that of SAPK3 as shown in Example 4. Both enzymes phosphorylated the transcription factors ATF2, Elk-1 and SAP-1 at similar rates, but were far less effective than SAPK2a (also called RK/p38) or SAPK2b (also called p38p) in activating MAPKAP kinase-2 and MAPKAP kinase-3. Unlike SAPK1 (also called JNK), SAPK3 and SAPK4 did not phosphorylate the activation domain of c-Jun. Unlike SAPK2a and SAPK2b, SAPK4 and SAPK3 were not inhibited by the drugs SB 203580 and SB 202190. Our results suggest that cellular functions previously attributed to SAPK1 and/or SAPK2 may be mediated by SAPK2 or SAPK4.

Materials and Methods

Materials

SB 203580 and SB 202190 were generous gifts from Dr John Lee (SmithKline Beecham, King of Prussia, Pa., USA) and dissolved in DMSO. Anti-MKK6 antibodies (raised against the peptide CNPGLKEAFEQPQTS corresponding to a sequence near the N-terminus of human MKK6) were generated and purified as described previously (Cuenda et al, 1996; Meier et al, 1996). MalE-Mpk2, the Xenopus homologue of SAPK2a (Rouse et al, 1994) and rat GST-SAPK3 (Example 4 and Cuenda et al, 1997) were expressed in E. coli and purified as described previously. Sources of all other materials, enzymes, fusion proteins and methods are given in Example 4 or Cuenda et al (1997).

cDNA Cloning and Sequencing

The NotI/EcoRI insert from EST clone 156272 (GenBank number R72662), which encodes a portion of SAPK2b (p38β, Jiang et al, 1996), was used as the probe to screen a human pituitary gland cDNA library (Clontech, Palo Alto, Calif.) at high-stringency. Several partial ERK5 clones, a number of SAPK2b clones, some of which were full-length, and one partial SAPK4 clone were obtained after screening 2×10⁶ phage. Following sequencing, the SAPK4 insert was used as the probe to screen the pituitary gland cDNA library under high-stringency conditions. A total of 16 hybridisation-positive clones was obtained after screening 3×10⁶ plaques; they were isolated, the EcoRI inserts subcloned into M13mp18 and sequenced. Three of the 16 clones were full-length. Sequencing was performed both manually using synthetic oligonucleotides as primers and on an Applied Biosystems 377 DNA sequencer with fluorescent primers. Full-length sequence was compiled from both strands of cDNA clone hSAPK412. The NCBI sequence databases were searched using the blast algorithm (blast@ncbi.nlm.nih.gov). A multiple alignment of SAPK4, SAPK3, SAPK2a, SAPK2b and HOG1 was built up by eye.

RNA Blot Analysis

RNA blots were performed using human multiple tissue Northern blots from Clontech with 2 µg poly(A)⁺ RNA per lane. Probes were labelled with [³²P] dCTP by random priming and hybridised under high-stringency conditions. The SAPK4 probe was prepared from the gel-purified insert of cDNA clone hSAPK412. The human P-actin probe was purchased from Clontech.

SAPK2b, SAPK3 and SAPK4 Expression Plasmids

For bacterial expression, the open reading frames of human cDNA clones hSAPK2B2, hSAPK32 and hSAPK412 were amplified by PCR and subcloned as EcoRI fragments into expression vector pGEX4T-1 (Pharmacia), followed by transformation into *E. coli* strain BL21(DE3). The transformed bacteria were grown to an absorbance of 0.6 at 600 nm and induced with 0.4 mM isopropyl-1-thio-β-galactopyranoside (IPTG). Human GST-SAPK2b, GST-SAPK3 and GST-SAPK4 were purified by affinity chromatography on glutathione-agarose. For expression of c-myc epitope-tagged SAPK4, PCR was used to introduce the nucleotide sequence encoding the amino acid sequence MEQKLISEEDLN (SEQ. ID. NO: 4) at the carboxy-terminus of SAPK4, followed by a stop codon. The resulting EcoRI/NotI fragment was subcloned into the mammalian expression vector pcDNA3.1 (Invitrogen). Substitution of Asp-168 by Ala in SAPK4 to produce a kinase-inactive mutant was performed by site-directed mutagenesis. PCR fragments were verified by DNA sequencing. Transfections into COS1 cells were done as described in Example 4 and Cuenda et al, 1997.

SAPK4, SAPK2a and SAPK2b were assayed routinely by the phosphorylation of MBP, exactly as described for SAPK3 in Example 4 and Cuenda et al, 1997. One unit of activity was that amount of enzyme which incorporated 1 nmol of phosphate into MBP in 1 min. SAPK4 activators were assayed by their ability to activate GST-SAPK4, as described for GST-SAPK3 in Example 4 and Cuenda et al, 1997. Control experiments were carried out in which GST-SAPK4 was omitted. One unit of SAPK4 activator was that amount which increased SAPK4 activity by I U/min. MAPKAP-K2 and MAPKAP-K3 were assayed using the peptide KKLNRTLSVA as substrate (Stokoe et al, 1993) and one unit of activity was that amount which catalysed the phosphorylation of 1 nmol of peptide substrate in one min. SAPK2a activators were assayed by their ability to activate the *X. laevis* homologue of SAPK2a (Meier et al, 1996). Activated SAPK2a itself was measured by the activation of GST-MAPKAP-K2(46400). 0.1% DMSO was present in all experiments where the effects of SB 203580 and SB 202190 were being studied. This concentration of DMSO inhibited each SAPK by about 10%.

Immunoprecipitation of SAPK4

Lysates of cells transfected with myc epitope-tagged SAPK4 were centrifuged at 4° C. for 10 min at 13000×g. Aliquots of the supernatant (100 µg protein) were incubated for 2 h on a shaking platform with 5 µl of protein G-Sepharose coupled to 3 µg of monoclonal antibody 9E10 which recognises the c-myc epitope The imrnunoprecipitates were washed and assayed as described in Example 4 and Cuenda et al, 1997.

Results

Molecular Cloning of Human SAPK4

To identify novel members of the SAPK family, we used EST clone 156272 (GenBank number R72662), which encodes a portion of SAPK2b (p38p), as the probe to screen a human pituitary gland cDNA library. Sequencing of positive clones showed three distinct sequences. The first set of clones encoded portions of ERK5 (Zhou et al, 1995) [also called BMK1 (Lee et al, 1995)], whereas the second set encoded a novel form of p38β (see Discussion). The third set of clones encoded a protein whose sequence was similar to, but differed from that of known SAPKs and which was consequently named stress-activated protein kinase4 (SAPK4). The nucleotide and deduced amino acid sequence of human SAPK4 is shown in FIG. 1. An open reading frame encodes a protein of 365 amino acids, with a predicted molecular mass of 42 kDa. It possesses the conserved amino acid domains (I–XI) characteristic of protein kinases and shows 64% sequence identity with SAPK3, 59% identity with SAPK2a, 58% identity with SAPK2b, 42% identity with HOG1 from *S. cerevisiae* (FIG. 2), 45% identity with SAPK1 and 41% identity with p42 MAP kinase. Residues Thr180 and Tyr182 in subdomain VIII are in an equivalent position to the TEY, TPY and TGY sequences in known MAP kinases and SAP kinases, phosphorylation of which is required for enzymatic activity. SAPK4 shares a TGY sequence with SAPK2a, SAPK2b, SAPK3 and HOG1 (FIG. 2). Moreover, as in SAPK2a, SAPK2b, SAPK3 and HOG1, subdomain VII is separated by only 6 amino acids from the activation region in subdomain VIII (FIG. 2), whereas this gap is 8 residues in SAPK1 and over 12 residues in MAP kinases. The tissue distribution of SAPK4 mRNA in human tissues was assessed by RNA blotting (FIG. 3). Hybridisation of [³²P]-labelled SAPK4 cDNA to multiple tissue Northern blots showed a transcript of approximately 2.3 kb which was present in most of the sixteen tissues examined, albeit at variable levels (FIG. 3). Highest levels were detected in pancreas, testis, small intestine and prostate gland. Hybridisation of the blots with a probe for β-actin showed approximately equal loading of RNA (data not shown).

SAPK4 is Activated by Cellular Stresses and Cytokines

SAPK4 is most closely related to SAPK3, SAPK2a and SAPK2b, enzymes that are activated by cellular stresses and the cytokines IL1 and TNF as described above. We therefore investigated whether the same stimuli would activate SAPK4. Human epithelial KB cells were transiently transfected with a myc epitope-tagged SAPK4 and, after exposure to cellular stresses or cytokines, the enzyme was imunoprecipitated and assayed. These experiments showed that the stimuli which trigger the activation of SAPK2a, SAPK2b or SAPK3 also activate SAPK4 (FIG. 4), while stimuli that do not activate SAPK2a, SAPK2b or SAPK3 (such as insulin-like growth factor-1 (IGF-1) and phorbol esters] also failed to activate SAPK4 (FIG. 4).

Identification of SKK3 as the Major Activator of SAPK4 in Epithelial Cells

We have shown previously that SKK3 accounts for 95% and SKK2 for 5% of the SAPK2a activator detected after Mono S chromatography of lysates from KB cells that have been stressed in several ways or stimulated with IL1 (Cuenda et al, 1996; Meier et al, 1996). As shown in FIG. 5, the single peak of SAPK4 activator detected after subjecting KB cells to IL1 or the protein synthesis inhibitor anisomycin co-migrated with SKK3 on Mono S and was immunoprecipitated quantitatively and specifically by anti-MKK6 antibodies. This experiment also demonstrated that SKK4 and SKK5, which are activated in KB cells by these stimuli, and which elute from Mono S at a higher NaCl concentration than SKK3 (Meier et al, 1996), do not activate SAPK4. SKK3 was also the only activator of SAPK4 after subjecting KB cells to osmotic stress using sorbitol (data not shown). Further evidence that SKK3 can activate SAPK4 in vivo was obtained by co-transfection into COS cells. SAPK4 activity was elevated 12.5±0.63-fold by co-expression with SKK3 (n=3). In contrast, SAPK4 was not activated significantly by co-transfection with MEK kinase, under conditions where MEK kinase activated the endogenous SKK1 in COS cells (data not shown).

Activation of SAPK4 by SKK3 in vitro

SAPK4 was activated in vitro by a highly purified preparation of SKK3 from skeletal muscle (FIG. 6), but could not be activated by MKK1 under conditions where p42 MAP kinase was activated maximally (data not shown). The activation of SAPK4 by SKK3 occurred two- to three-fold more slowly than that of SAPK2a, although both enzymes attained the same specific activity towards myelin basic protein (MB P) after 2 h (FIG. 6A). The activity of SAPK2a and SAPK4 towards MBP is 25–50 fold lower than the activity of p42 MAP kinase towards this substrate (Stokoe et al, 1992a). The activation of SAPK4, like that of SAPK3 (Example 4 and Cuenda et al, 1997), reached a plateau at ~1.6 mol/mol subunit (data not shown) and was accompanied by the appearance of phosphotyrosine and phosphothreonine in similar amounts (FIG. 6B). Interestingly, SAPK4, like SAPK3 but unlike SAPK2a, also became phosphorylated at a serine residue(s). This did not occur when wild-type SAPK4 was replaced by the catalytically inactive SAPK4-D168A mutant (FIG. 7B), indicating that serine phosphorylation is catalysed by SAPK4 itself after it has been activated. Interestingly, the inactive SAPK4 mutant could only be phosphorylated on tyrosine and not on threonine, indicating that this mutation induces a conformational change that affects the recognition of SAPK4 by SKK3.

Activation of SAPK4 by SKK1 (MKK4) in Vitro

SAPK2 is not only phosphorylated by SKK2 and SKK3 in vitro, but also by SKK1 (MKK4) (see above). SKK1 is activated by cytokines and cellular stresses and it was therefore of interest to investigate whether this enzyme also had the potential to activate SAPK4 in vitro. FIG. 7 shows that SAPK4 is phosphorylated and activated by SKK1 in vitro, but at a much slower rate than SAPK2a under identical conditions. Consistent with this slow rate of activation, SAPK4 was not activated after co-transfection into COS1 cells with MEK kinase (data not shown), an upstream activator of SKK1. This is consistent with the negligible contribution of SKK1 to the SAPK4-activating activity in KB cell extracts (FIG. 5).

Comparison of the Substrate Specificity of SAPK4 With that of SAPK2a, SAPK2b and SAPK3

SAPK4 was more active than SAPK2a or SAPK2b in phosphorylating fusion proteins with glutathione S-transferase (GST) linked to the activation domains of the transcription factors Elk-1, ATF2, SAP-1, SAP-2 and p53, while c-Jun was only phosphorylated poorly by the three enzymes (Table 1). SAPK4 was far less effective than SAPK2a in activating GST-MAPKAP-K2(5–400) and full-length GST-MAPKAP-K3, the initial rate of activation of MAPKAP-K2 and MAPKAP-K3 and the half-time for maximal activation being 20 times slower (FIG. 8). The specificity of SAPK4 in vitro was similar to that of SAPK3 (Table 1; Example 4 and Cuenda et al, 1997). Consistent with their similar amino acid sequences (FIG. 2), the substrate specificities of SAPK2a and SAPK2b were virtually indistinguishable (Table 1, FIG. 8).

Table 1. Comparison of the Substrate Specificities of SAPK4 With Those of SAPK2a, SAPK2b and SAPK3

Experiments were carried out with the Xenopus homologue of SAPK2a, human SAPK2b and human SAPK4. The SAPKs were activated in vitro (FIG. 7) and phosphorylation of each protein was studied at a SAPK concentration of 0.15 U/ml. The results are presented as means±SEM of six determinations (two separate experiments). The data for rat SAPK3 are taken from Example 4 and Cuenda et al (1997).

|  | Rates of phosphorylation relative to MBP (%) | | | |
| --- | --- | --- | --- | --- |
| Substrate (1 µm) | SAPK2a | SAPK2b | SAPK3 | SAPK4 |
| MBP | 100 | 100 | 100 | 100 |
| Elk-1 | 90 ± 10 | 136 ± 12 | 181 ± 30 | 175 ± 25 |
| ATF2 | 40 ± 2 | 62 ± 2 | 107 ± 20 | 130 ± 2 |
| SAP-1 | 25 ± 1 | 27 ± 5 | 108 ± 15 | 62 ± 5 |
| MAPKAP-K2 | 90 ± 5 | 83 ± 3 | 25 ± 3 | 28 ± 5 |
| MAPKAP-K3 | 87 ± 10 | 66 ± 6 | 20 ± 6 | 18 ± 2 |
| p53 | 15 ± 3 | 29 ± 2 | 30 ± 1 | 13 ± 1 |
| SAP-2 | 13 ± 1 | 18 ± 4 | 20 ± 3 | 8 ± 2 |
| c-Jun | 4 ± 1 | 7 ± 2 | 2 ± 1 | 6 ± 2 |

SAPK4 is not Inhibited by SB 203580 or SB 202190

Like SAPK3, bacterially expressed SAPK4 that had been activated by SKK3 in vitro was not inhibited by SB 203580 or SB 202190 (FIG. 9). In contrast, SAPK2a and SAPK2b were inhibited by both drugs with similar $IC_{50}$ values of 0.3–0.6 µM (FIG. 9). SB 203580 and SB 202190 also failed to inhibit the dephosphorylated forms of SAPK3 and SAPK4 which have <0.1% of the activity of the phosphorylated forms (data not shown). In addition, SB 203580 did not prevent the activation of transfected SAPK3 by osmotic shock in KB cells.

Discussion

In this Example we report the cloning of the cDNA encoding human SAPK4, a novel MAP kinase family member whose mRNA is widely expressed and whose amino acid sequence is about 60% identical to SAPK2a, SAPK2b and SAPK3. Moreover, SAPK4, like SAPK2a, SAPK2b and SAPK3, contains the dual TGY phosphorylation motif and a six amino acid insertion between subdomain VII and the activation loop in subdomain VII. SAPK4 is less similar to SAPK1 (45% identity) and p42/p44 MAP kinases (41% identity). During the course of this study, we have also sequenced several cDNA clones for SAPK2b. They were found to encode a protein of 364 amino acids that differs from the published p38β sequence (Jiang et al, 1996) in two respects. It lacks an eight amino acid sequence between kinase subdomains V and VI and it shows two amino acid differences in this region. As a result, our SAPK2b sequence aligns with the other SAP kinase sequences without requiring any gaps.

Consistent with its amino acid sequence similarity to SAPK2a, SAPK2b and SAPK3, SAPK4 is activated in response to the same cellular stresses and cytokines. The only activator of SAPK4 that could be detected in extracts prepared from epithelial KB cells exposed to a cellular stress or IL1 was SKK3, the product of the MKK6 gene. SAPK4 also became activated when co-transfected with SKK3 DNA into COS cells. In contrast, SAPK4 was activated poorly by SKK1 (MKK4) in vitro and was not activated in co-transfection experiments with MEK kinase, an upstream activator of SKK1 (Yan et al, 1994). SAPK4 was also not activated by MKK1, SKK2 (MKK3), SKK4 or SKK5. Thus, SKK3 which is the dominant activator of SAPK2a (Cuenda et al, 1996), SAPK2b (Jiang et al, 1996) and SAPK3 (Example 4 and Cuenda et al, 1997) in several mammalian cell lines, also appears to be the major activator of SAPK4.

In contrast to SAPK2a and SAPK2b, which are inhibited by SB 203580 or SB 202190 at submicromolar concentrations, SAPK3 and SAPK4 were not affected by these drugs; moreover, SB 203580 did not inhibit the activation of SAPK3. The failure of SB 202190 to inhibit SAPK3 is in disagreement with the work of Li et al (1996) who reported that the basal activity of bacterially expressed SAPK3 was inhibited by this drug. The reason for this discrepancy is unclear, because we failed to find any effect of SB 203580 or SB 202190 on either the basal activity of expressed SAPK3 or on SAPK3 that had been maximally activated by phosphorylation with SKK3. Identical results were obtained using bacterially expressed rat SAPK3 (Example 4 and Cuenda et al, 1997) and human SAPK3.

The substrate specificity of SAPK4 in vitro resembled that of SAPK3 in that, while both enzymes phosphorylated a number of proteins (including the activation domains of several transcription factors) at similar rates to SAPK2a and SAPK2b, they were far less effective in activating MAPKAP-K2 and MAPKAP-K3 than either SAPK2a or SAPK2b. The last mentioned result is consistent with the finding that SB 203580 suppresses the stress- and cytokine-induced activation of MAPKAP-K2 and MAPKAP-K3 by 80–95% in every mammalian cell so far examined (Cuenda et al, 1995; Beyaert et al, 1996; Clifton et al, 1996; McLaughlin et al, 1996). Moreover, although SAPK3 and SAPK4 phosphorylate the activation domain of the transcription factor Elk-1 efficiently in vitro, neither enzyme appears to be rate-limiting for Elk-1 phosphorylation in vivo, because Elk-1 phosphorylation induced by cellular stresses can be prevented by SB 203580 in fibroblast cell lines (Hazzalin et al, 1996) or by a combination of SB 203580 and PD 98059 in HeLa cells (Price et al, 1996). PD 098059, a specific inhibitor of the activation of MKK1 (Alessi et al, 1995a), prevents the activation of p42/p44 MAP kinases. Candidates as physiological substrates for SAPK3 and SAPK4 are proteins whose phosphorylation/activation triggered by cellular stresses and/or pro-inflammatory cytokines is not prevented by SB 203580. Such proteins include the transcription factors c-Jun, ATF2 and NFKB (Beyaert et al, 1996; Hazzalin et al, 1996). However, c-Jun is phosphorylated very poorly by SAPK3 and SAPK4 and isoforms of SAPK1 are likely to phosphorylate this protein in vivo (see Introduction).

In summary, the number of MAP kinase family members which are activated by cellular stresses and/or pro-inflammatory cytokines is much greater than was realised previously (shown schematically in FIG. 10). In addition to SAPK1, SAPK2a, SAPK2b, SAPK3 and SAPK4, the p42/p44 MAP kinases, which are strongly activated by growth factors, are also activated by stressful stimuli and pro-inflammatory cytokines in some cellular backgrounds, albeit more weakly. Moreover, the MAP kinase family member ERK5 (also called BMK1) is activated by osmotic and oxidative stresses (Abe et al, 1996). The development of specific inhibitors for each of these MAP kinase family members would greatly facilitate the elucidation of their physiological roles.

EXAMPLE 2

Protein Kinase Assays

SAPK4 is assayed routinely by the phosphorylation of MBP. SAPK4 (0.5 or 1 $\mu$M) in 40 $\mu$l of 25 mM Tris-HCl pH 7.5, 0.1 mM EGTA, 0.1 mM sodium orthovanadate, 1 $\mu$M PKI and 0.33 mg/ml MBP is incubated for 3 min at 30° C. before initiating the reaction with 10 $\mu$l of 50 mM magnesium acetate –0.5 mM [$\gamma$-$^{32}$P]ATP. After 20 min at 30° C., 40 $\mu$l aliquots are withdrawn, spotted on to 1.5×1.5 cm squares of Whatman P81 phosphocellulose paper and immersed in 75 mM phosphoric acid. After washing and drying the papers (Alessi et al, 1995 *Meth. Enzymol.* 255, 279–290) $^{32}$P radioactivity incorporated into MBP is measured. One unit of activity is that amount of enzyme which incorporated 1 nmol of phosphate into MBP in 1 min.

SAPK4 activators are assayed by their ability to activate GST-SAPK4. A 15 $\mu$l Mono S fraction is incubated for 3 min at 30° C. with 2.5 $\mu$l of 10 $\mu$M GST-SAPK4 in 50 mM Tris-HCl pH 7.5, 0.1 mM EGTA, 0.03% (by mass) Brij-35, 0.1% (by vol) 2-mercaptoethanol and 5% (by vol) glycerol, and the reaction is initiated with 2.5 $\mu$l of 80 mM magnesium acetate –0.8 mM unlabelled ATP. After 30 min, an aliquot (10 $\mu$l) is withdrawn and assayed for SAPK4 activity as described above. Control experiments are carried out in which GST-SAPK4 is omitted from the incubation mixture. One unit of SAPK4 activator is that amount which increased the activity of SAPK4 by 1 U/min.

MAPKAP-K2 and MAPKAP-K3 are assayed using the peptide KKLNRTLSVA as substrate (Stokoe et al, 1993 *Biochem J.* 296, 843–849) and one unit of activity is that amount which catalyses the phosphorylation of 1 nmol of peptide substrate in 1 min. SAPK2 is measured by the activation of GST-MAPKAP-K2 (4–400) and SAPK-2 activators by their ability to activate MalE-Mpk2 (the Xenopus homologue of SAPK2) (Meier et al, 1996 *Eur. J. Biochem.* 236, 796–805).

EXAMPLE 3

Activation and Stoichiometric Phosphorylation of GST-SAPK4 by SKK3 and SKK1

The incubations contain 25 mM Tris-HCl, pH 7.5, 0.1 mM EGTA, 1 $\mu$M PKI, 0.1% (by vol) 2-mercaptoethanol, 0.5 $\mu$M GST-SAPK4 purified SKK3 or SKK1 (100 U/ml, see Cuenda et al, 1996 *EMBO J.* 15, 4156–4164 for definition of units), 10 mM magnesium acetate and 0.1 mM ATP. The reaction is initiated with MgATP after pre-incubating the other components for 3 min at 30° C. At various times, aliquots are removed and assayed for SAPK4 activity as described above in Example 2. To determine the extent of phosphorylation of SAPK4, parallel incubations were carried out in which unlabelled ATP was replaced by [$\gamma$-$^{32}$P] ATP (2×10$^6$ cpm/nmol). At various times, aliquots of the reaction are added to a 1 ml of 20% (by mass) trichloroacetic acid (TCA). After centrifugation for 5 min at 13 000 g, the supernatant is discarded and the pellet is washed three times with 25% TCA and analysed by Cereakov counting. Phosphorylation stoichiometries are determined using the calculated molecular masses of each fusion protein and the protein concentration determined according to Bradford (1976) *Anal. Biochem.* 72, 248–254.

EXAMPLE 4

Characterisation of SAPK3

Materials and Methods

Materials. Tissue culture reagents, microcystin-LR, Lipfectin reagent, MBP and human IG-1 were purchased from Gibco-BRL (Paisley, UK), Protein G-Sepharose from Pharmacia (Milton Keynes, UK), and recombinant human IL-1α and EGF from Boehringer; anisomycin, sorbitol and TNFα from Sigma (Poole, UK). PKI, the specific peptide inhibitor of cAMPdependent protein kinase (TTYADFIASGRTGRRNAIHD) and all other peptides were synthesized by Mr F B Caudwell in the MRC Protein Phosphorylation Unit. SB 203580, a generous gift from Dr J Lee (SmithKline Beecham, King of Prussia, USA) was dissolved in dimethylsulphoxide to give a final concentration of 20 mM. Other reagents were of analytical grade or better, and purchased from BDH Chemicals or Sigma Chemical Co (Poole, UK).

Enzymes and transcription factors. SKK3 was purified from rabbit skeletal muscle (Cuenda et al, 1996). *E. coli* plasmids encoding glutathione S-transferase (GST) fusion proteins were kindly provided by the investigators shown in parentheses, expressed in *E. coli* and purified by affinity chromatography on glutathione-Agarose; GST-MAPKAP-K2(5–400) and GST-MAPKAP-K2(46–400) (Dr R Ben-Levy and Dr C Marshall, Institute for Cancer Research, London, Ben Levy et al, 1995), GST-MAPKAP-K3 (Dr J Young, SmithKline Beecham, King of Prussia, USA), GST-MKK1 (Dr C Marshall), GST-MKK4 (Dr J Woodgett, Ontario Cancer Institute, Canada), GST-SAP1(267–431), GST-SAP2(221–417), GST-Elk1(307–428), GST-cJun(1-194), GST-ATF2(19–96) and various derivatives of GST-ATF2(19-96) in which Thr-69, Thr-71 and/or Ser-90 were mutated to Ala (Drs N Jones and R Treisman, ICRF, London) MalE fusion proteins expressing the C-terminal kinase domain of MEK kinase (MalE-MEKK) and the Xenopus homologue of SAPK2 (MalE-Mpk2) were generous gifts from Dr A R Nebreda (EMBL, Heidelberg, Germany). DNA expressing the C-terminal kinase domain of MEK kinase for transfection studies (Olson et al, 1995) was provided by Dr A Ashworth (Institute of Cancer Research, London). p53 (Helps et al, 1995) was provided by Dr N Helps in the MRC Protein Phosphorylation Unit.

SAPK3 and SKK3 expression plasmids. For bacterial expression the open reading frame of cDNA clone rSAPK37 (Mertens et al, 1996) was amplified by PCR and subcloned as an EcoRI fragment into expression vector pGEX-4T1 (Pharmacia), followed by transformation into *E. coli* strain BL21 (DE3). The transformed bacteria were grown to an absorbance of 0.6 at 600 nm and induced with 0.4 mM isopropyl-1-thio-b-galactopyranoside (IPTG). GST-SAPK3 was purified by affinity chromatography on glutathione-agarose. For transfections, the open reading frame of cDNA clone rSAPK37 was amplified by PCR and subcloned as an EcoRI fragment into the mammalian expression vector pSG5 (Stratagene). Alternatively, PCR was used to introduce a nucleotide sequence encoding the c-myc tag MEQK-LISEEDLN (SEQ. ID. NO: 4) at the carboxy-terminus of rSAPK3, followed by a stop codon. The resulting fragment was then ligated into pSG5. A bacterial expression construct encoding human SKK3 (Cuenda et al, 1996) was a kind gift from Dr A R Nebreda (EMBL, Heidelberg, Germany). The open reading frame of human SKK3 was amplified by PCR and subcloned as a HindIII fragment in the mammalian expressing plasmid pcDNA3.1 (Invitrogen). Substitution of Asp171 by Ala in SAPK3 to produce a kinase-inactive mutant was performed by site-directed mutagenesis. PCR fragments were verified by DNA sequencing.

Cell culture and transient transfections. 293, KB and COS-7 cells were cultured in Dulbecco's modified Eagles' Medium (DMEM) supplemented with 10% foetal calf serum, at 37° C., in an atmosphere of 5% $CO_2$. Transfections of 293 cells were carried out using the calcium-phosphate method. Cells were split to a density of 2×106 per 10 cm dish, and after 12 h at 37° C., 10 μg of plasmid DNA in 0.45 ml of sterile water was added to 50 μl of sterile $CaCl_2$, and then 0.5 ml of sterile buffer composed of 50 mM N,N-bis [2-hydroxyethyl]-2-aminoethanesulphonic acid/HCl pH 6.96, 0.28 M NaCl and 1.5 mM $Na_2HPO_4$ was added. The resulting mixture was vortexed for 1 min, allowed to stand at room temperature for 20 min, and then added dropwise to a 10 cm dish of 293 cells. The cells were placed in an atmosphere of 3% $CO_2$ for 16 h at 37° C., then the medium was aspirated and replaced with new DMEM containing 10% foetal calf serum. The cells were incubated for 24 h at 37° C. in an atmosphere of 5% $CO_2$ before stimulation. Plasmid DNA was transfected into KB cells and COS-1 cells by the lipofectin method as recommended by the suppliers. After splitting cells to a density of 1×10⁶ per 6 cm dish and incubation for 24 h at 37° C. in an atmosphere of 5% $CO_2$, the cells were washed once with 2 ml of serum-free growth medium and 2 μg of DNA (previously incubated for 15 min at room temperature with 15 mg lipofectin-reagent) was added. After 6 h at 37° C. in an atmosphere of 5% $CO_2$, the DNA containing medium was replaced with new DMEM containing 10% foetal calf serum. After a further 48 h, the cells were stimulated with the agonists indicated in the figure legends. Cells were incubated in DMEM for 12 h in the absence of serum before stimulation with IGF-1 or for 1 h before exposure to other stimuli. Cells were lysed as described (Rouse et al, 1994), except that 2 μM microcystin was present in the lysis buffer.

Protein kinase assays. SAPK3 was assayed routinely by the phosphorylation of MBP. SAPK3 (0.5 or 1 μM) in 40 μl of 25 mM Tris/HCl pH 7.5, 0.1 mM EGTA, 0.1 mM sodium orthovanadate, 1 μM PKI and 0.33 mg/ml MBP was incubated for 3 min at 30° C. before initiating the reaction with 10 μl of 50 mM magnesium acetate-0.5 mM [γ-$^{32}$P]ATP. After 20 min at 30° C. 40 μl aliquots were withdrawn, spotted on to 1.5×1.5 cm squares of Whatman P81 phosphocellulose paper and immersed in 75 mM phosphoric acid. After washing and drying the papers (Alessi et al, 1995b), $^{32}$P radioactivity incorporated into MBP was measured. One unit of activity was that amount of enzyme which incorporated 1 nmol of phosphate into MBP in 1 min.

SAPK3 activators were assayed by their ability to activate GST-SAPK3. 15 ml Mono S fraction was incubated for 3 min at 30° C. with 2.5 μl of 10 μM GST-SAPK3 in 50 mM Tris/HCl pH 7.5, 0.1 mM EGTA, 0.03% (by mass) Brij-35, 0.1% (by vol) 2-mercaptoethanol and 5% (by vol) glycerol, and the reaction was initiated with 2.5 μl of 80 mM magnesium acetate-0.8 mM unlabelled ATP. After 30 min, an aliquot (10 μl) was withdrawn and assayed for SAPK3 activity as described above. Control experiments were carried out in which GST-SAPK3 was omitted from the incubation mixture. One unit of SAPK3 activator was that amount which increased the activity of SAPK3 by 1 U/min. MAPKAP-K2 and MAPKAP-K3 were assayed using the peptide KKLNRTLSVA as substrate (Stokoe et al, 1993) and one unit of activity was that amount which catalysed the phosphorylation of 1 nmol of peptide substrate in one min. SAPK2 was measured by the activation of GST-MAPKAP-K2(46–400) and SAPK2 activators by their ability to activate MalE-Mpk2 (the Xenopus homologue of SAPK2) (Meier et al, 1996).

Activation and stoichiometric phosphorylation of GST-SAPK3 and MalE-Mpk2 by SKK3 and SKK1. The incubations contained 25 mM Tris/HCl, pH 7.5, 0.1 mM EGTA, 1 mM PKI, 0.1% (by vol) 2-mercaptoethanol, 0.5 mM GST-SAPK3 or MalE-Mpk2, purified SKK3 or SKK1 (100 U/ml, see Cuenda et al, 1996 for definition of units), 10 mM magnesium acetate and 0.1 mM ATP. The reaction was initiated with MgATP after preincubating the other components for 3 min at 30° C. At various times aliquots were removed and assayed for SAPK3 or SAPK2 activity as described above. To determine the extent of phosphorylation of SAPK3 and SAPK2, parallel incubations were carried out in which unlabelled ATP was replaced by [$\alpha$-$^{32}$P] ATP (2×20 10$^6$ cpm/nmol). At various times, aliquots of the reaction were added to a 1 ml of 20% (by mass) trichloroacetic acid (TCA). After centrifugation for 5 min at 13000×g, the supernatant was discarded and the pellet washed three times with 25% TCA and analysed by Cerenkov counting. Phosphorylation stoichiometries were determinated using the calculated molecular masses of each fusion protein and the protein concentration determined according to Bradford (1976).

Immunoprecipitation of SAPK3. Lysates of cells transfected with SAPK3 were centrifuged at 4° C. for 10 min at 13000×g. Aliquots of the supernatant (100 $\mu$g protein) were incubated for 120 min on a shaking platform with 5 ml of protein G-Sepharose coupled to either 3 $\mu$g of 9E10 monoclonal antibody which recognises the myc epitope (for myc-epitope tagged SAPK3) or 5 $\mu$g of affinity purified polyclonal antibody raised in sheep against the C-terminal sequence of rat SAPK3 (KPPRNLGARVPKETAL; SEQ. ID. NO: 5)(for untagged SAPK3). The suspension was centrifuged for 1 min at 13000×g, and the pellet washed twice with 1 ml of lysis buffer containing 0.5 M NaCl, and twice with lysis buffer, and the immunoprecipitate assayed for SAPK3 activity as described above, except that the reactions were carried out on a shaking platform to ensure that the Agarose beads remained in suspension and therefore had access to the substrate.

Antibodies and immunoprecipitation of SAPKKs. Polyclonal anti-MKK3 antibodies (raised against the peptide RNLDSRTFITIGDRN corresponding to a sequence near the N-terminus of MKK3), anti-MKK4 antibodies (raised against the peptide EQMPVSPSSPMYVD corresponding to the C-terminal 14 residues of XMEK2) and anti-MKK6 antibodies (raised against the peptide CNPGLKEAF-EQPQTS corresponding to a sequence near the N-terminus of human MKK6) were generated and purified as described previously (Cuenda et al, 1996; Meier et al, 1996). Aliquots (30 ml) of Mono S-purified SAPK2 activators or SAPK3 activator were incubated at 4° C. on a shaking platform with 5 ml of protein G-Sepharose coupled to 5 $\mu$g of anti-MKK3, 5 $\mu$l of anti-MKK4 or 2 $\mu$g of anti-MKK6 antibodies. After mixing for 90 min, the suspensions were centrifuged for 2 min at 13000 ×g and the supernatants assayed for SAPK3 activator. In control experiments, antibodies bound to protein G-Sepharose were incubated for 30 min at 4° C. with 50 mol of the appropriate peptide immunogen prior to immunoprecipitation.

Results

Figure 11A:
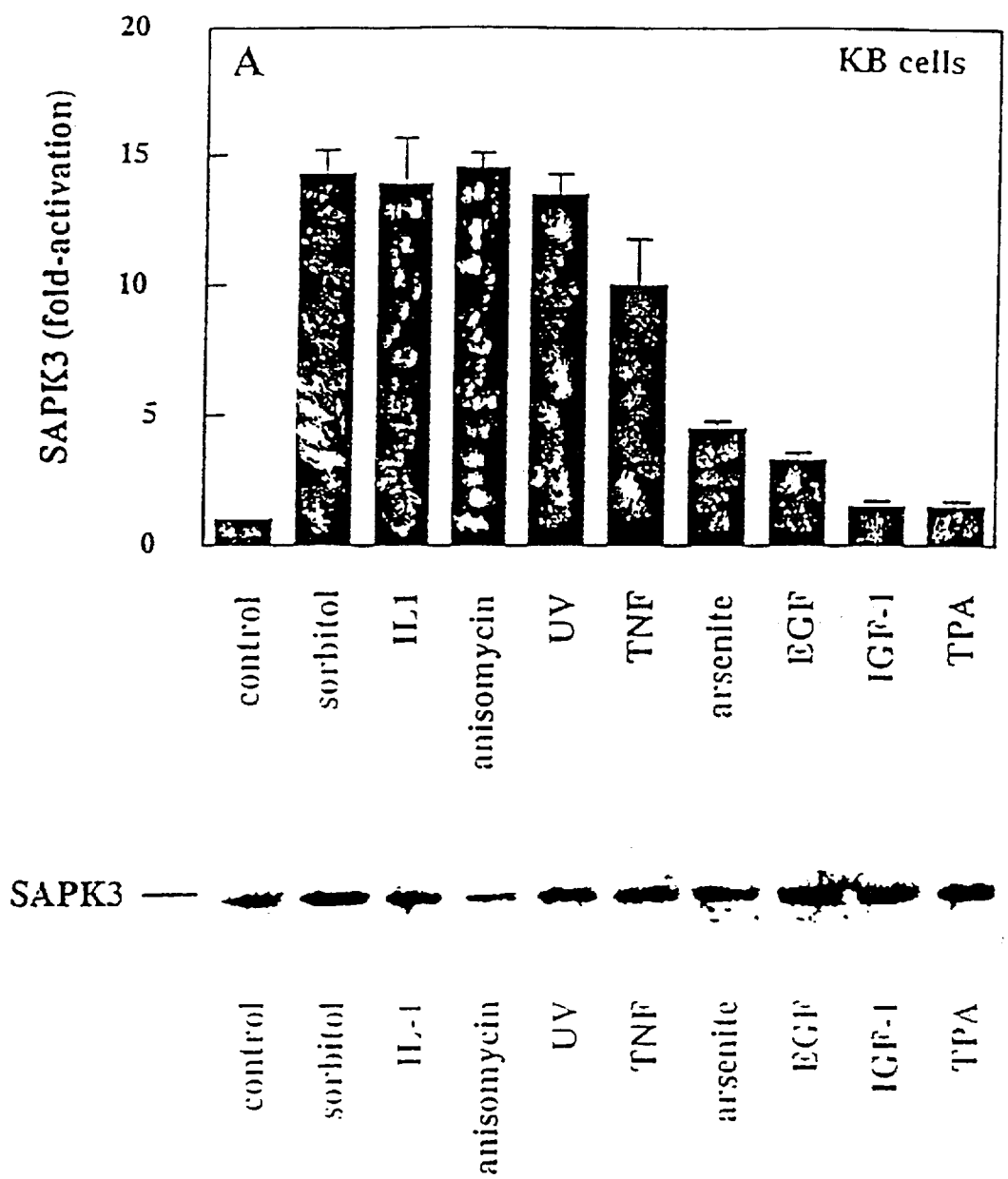
Figure 11B:
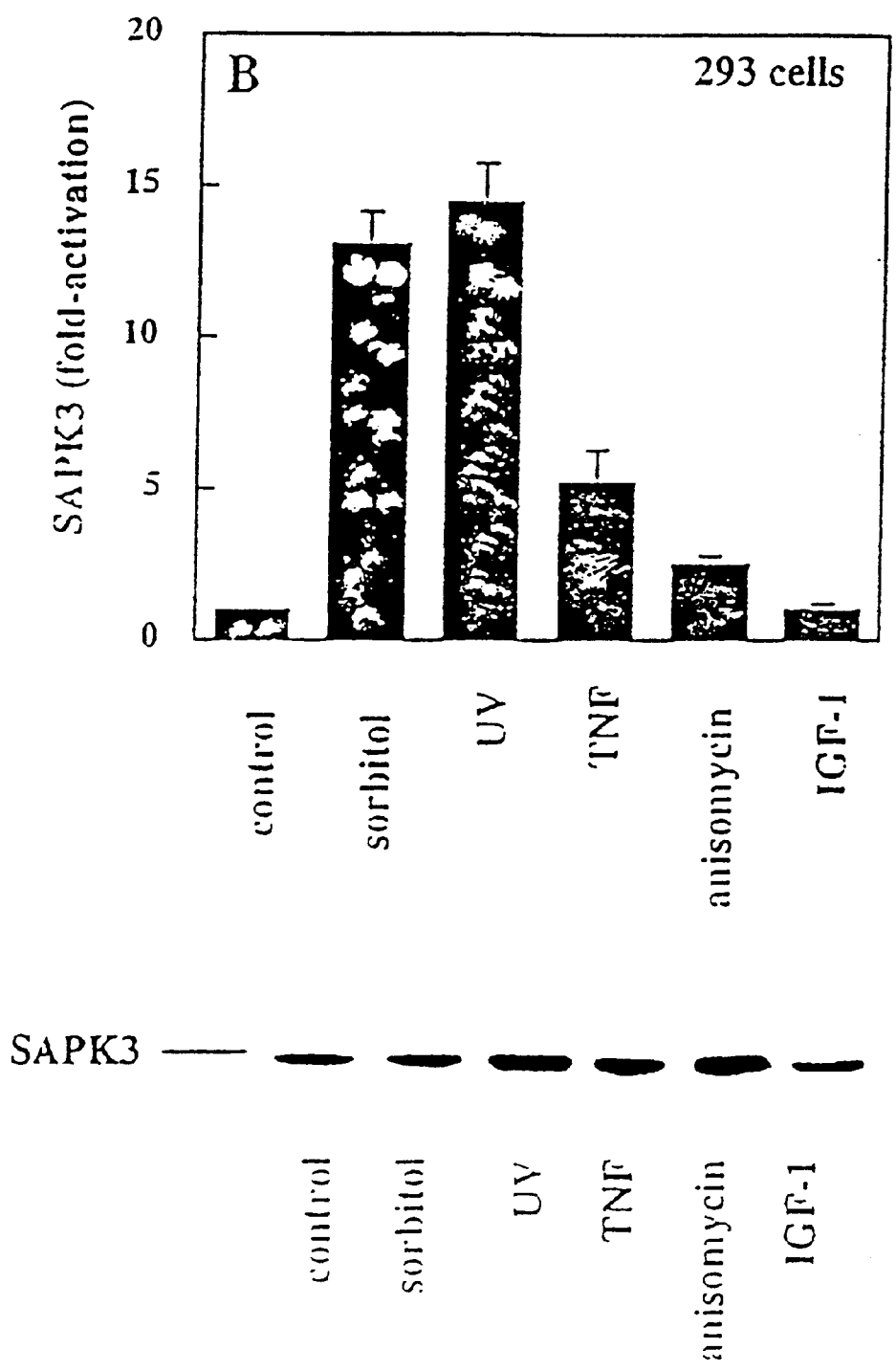

SAPK3 is activated by cellular stresses and cytokines. Human embryonic kidney epithelial 293 cells and human epithelial KB cells were transiently transformed with a myc epitope-tagged SAPK3 and, after exposure to cellular stresses or cytokines, the enzyme was immunoprecipitated and assayed. These experiments showed that the stimuli which trigger the activation of SAPK2 (or SAPK1) also activate SAPK3. Osmotic shock, the protein synthesis inhibitor inhibitor anisomycin, a chemical stress (sodium arsenite), UV-C irradiation, IL1 and TNF all activated SAPK3 5–14 fold (FIGS. 11A and 11B). Similar results were obtained when SAPK3 was transiently transfected into COS7 cells and then exposed to osmotic shock, anisomycin or sodium arsenite (data not shown). EGF activated transfected SAPK3 more weakly, while IGF-1 and phorbol esters caused little or no activation (FIG. 11A). In contrast, IGF-1 triggered a strong activation of transfected protein kinase B in parallel experiments (Alessi et al, 1996).

Identification of SKK3 as the major activator of SAPK3 in epithelial cells. Lysates from 293 cells that had been osmotically shocked for 15 min were chromatographed on Mono S and assayed for activators of SAPK2 and SAPK3. As reported previously for other mammalian cells (Cuenda et al, 1996; Meier et al, 1996), two peaks of SAPK2 activator were identified. The first eluted at the same position as SKK1 and SKK3 and the second at the same position as SAPKK2. Neither peak was observed in control experiments using lysates from unstimulated cells (FIG. 12A). The first peak of activity was SKK3 (or a very closely related homologue), because it was immunoprecipitated quantitatively by anti-MKK6 antibodies, but not by anti-MKK4 or anti-MKK3 antibodies (FIG. 12B). The second peak was immunoprecipitated by anti-MKK3 antibodies, but not by anti-MKK4 or anti-MKK6 antibodies (FIG. 12B). When the same fractions were assayed for activators of SAPK3 only a single peak was detected which coeluted with SKK3 (FIG. 12C) and was immunoprecipitated by anti-MKK6, but not by anti-MKK4 or anti-MKK3 antibodies (FIG. 12D). Identical results were obtained when the cells were stimulated with anisomycin (data not shown). No SAPK3 activator was observed in control experiments using lysates from unstimulated cells (FIG. 12C).

We have shown previously that SKK3 accounts for 95–100% of the SAPK2 activator detected after Mono S chromatography of lysates from KB cells that have been stressed in several ways or stimulated with IL-1 (Cuenda et al, 1996; Meier et al, 1996). As shown in FIG. 13, the single peak of SAPK3 activator detected after subjecting KB cells to osmotic shock or anisomycin comigrated with SKK3 on Mono S and was immunoprecipitated quantitatively and specifically by anti-MKK6 antibodies. This experiment also demonstrated that SAPKK4 and SAPKK5, which are also activated in KB cells by these stimuli, and which elute from Mono S at a higher NaCl concentration than SKK3 (Meier et al, 1996), do not activate SAPK3.

Further evidence that SKK3 can activate SAPK3 in vivo was obtained by cotransfection into COS cells. These experiments showed that SAPK3 activity was elevated 10-fold by coexpression with SKK3, and that exposure to osmotic shock triggered a 30-fold greater activation of transfected SAPK3 in cells where SKK3 had been cotransfected (FIG. 14).

Activation of SAPK3 by SKK3 in vitro. SAPK3 was activated in vitro by a highly purified preparation of SKK3 from skeletal muscle (FIG. 15), but could not be activated by MKK1 under conditions where p42 MAP kinase was activated maximally (data not shown). The rate of activation of SAPK3 by SKK3 was similar to that of SAPK2, and both enzymes attained the same specific activity towards myelin basic protein (MBP) after 1 h (FIGS. 15A and 15B). The activity of SAPK2 and SAPK3 towards MBP is 25–50 fold lower than the activity of p42 MAP kinase towards this substrate (Stokoe et al, 1992b). No activation or phosphorylation of SAPK2 or SAPK3 occurred when SKK3 was inactivated by protein phosphatase 2A prior to incubation with SAPK2 and SAPK3 (FIGS. 15A and 15B). The activation of SAPK2 and SAPK3 was accompanied by the appearance of phosphotyrosine and phosphothreonine as expected, both residues being phosphorylated to a similar extent at low or high levels of activation of SAPK3 and SAPK2 (FIG. 15C). Interestingly, SAPK3 (but not SAPK2) also became phosphorylated at a serine residue(s). This did not occur when wild type SAPK3 was replaced by inactive mutant (FIG. 15D), suggesting that serine phosphorylation is an autophosphorylation event catalysed by SAPK3 itself after it has been activated. The site of autophosphorylation is likely to be at Ser-3 and/or Ser-281, which are the only two serine residues in SAPK3 that are followed by proline (Mertens et al, 1996).

Activation of SAPK3 by SKK1 (MKK4) in vitro. SAPK2 is not only phosphorylated by SAPKK2 and SKK3 in vitro, but also by SKK1 (MKK4) (see Introduction). SKK1 is itself activated by cytokines and cellular stresses and it was therefore of interest to investigate whether this enzyme had the potential to activate SAPK3 in vitro. FIG. 16 shows that SAPK3 can be activated by SKK1 in vitro, but the initial rate of activation of SAPK3 is much slower than that of SAPK2 under identical conditions (FIG. 16A). Consistent with this slow rate of activation, SAPK3 was not activated after cotransfection in COS1 cells with MEK kinase (FIG. 14), an upstream activator of SKK1. This is consistent with the negligible contribution of SKK1 to the total SAPK3-activating activity observed in KB and COS cells.

Comparison of the substrate specificities of SAPK2 and SAPK3. SAPK3 was just as active as SAPK2 in phosphorylating the transcription factors Elk1, ATF2, SAP1, SAP2 and p53, while c-Jun was only poorly phosphorylated by both enzymes (Table 1). SAPK1 has been shown to phosphorylate ATF2 at Thr-69, Thr-71 and Ser-90 (Livingstone et al, 1995) and the phosphorylation of ATF2 by SAPK2 and SAPK3 was therefore studied in greater detail using wild type ATF2 and mutants in which these residues had been changed to Ala. Phosphoamino acid analysis showed that, after phosphorylation by SAPK3, wild-type ATF2 was phosphorylated on threonine and serine residues, the phosphothreonine content being twice as high as the phosphoserine content (data not shown). In contrast, after phosphorylation by SAPK2, ATF2 was only phosphorylated on threonine (data not shown). Consistent with these experiments, a mutant ATF2 in which Thr-69 and Thr-71 were changed to alanine was phosphorylated by SAPK3, but not by SAPK2 (FIG. 17) and phosphorylation of this mutant by SAPK3 occurred only on serine (data not shown). A mutant ATF2, in which Thr-69, Thr-71 and Ser-90 were all changed to Ala, was not phosphorylated by either SAPK2 or SAPK3, and a mutant in which Ser-90 was changed to Ala was phosphorylated at threonine residues by SAPK3, but not by SAPK2 (FIG. 17). These experiments indicate that SAPK2 and SAPK3 phosphorylate ATF2 at Thr69 and Thr-71, and that only SAPK3 phosphorylates Ser-90.

SAPK3 was far less effective than SAPK2 in activating GST-MAPKAP-K2(46–400) and full length GST-MAPKAP-K3, the initial rate of activation of MAPKAP-K2 and MAPKAP-K3 and the half time for maximal activation being 20 times slower (FIGS. 18A and 18B). We have reported previously that p42 MAP kinase can activate GST-MAPKAP-K2(46–400) in vitro, but cannot activate a nearly full length MAPKAP kinase-2 [GST-MAPKAP-K2(5–400)] (Ben-Levy et al, 1995). SAPK3 was also unable to activate GST-MAPKAP-K2(5–400) significantly (FIG. 18C).

SAPK3 is not inhibited by SB 203580. SAPK3 was not inhibited significantly by SB 203580, even at a concentration (0.1 mM) that was over 100-fold higher than the $IC_{50}$ for SAPK2 (0.6 $\mu$M) (FIG. 19).

Discussion

We have demonstrated that SAPK3 is activated in response to the same cellular stresses and cytokines as SAPK1 and SAPK2. In two epithelial cell lines, the only activator of SAPK3 that could be detected was SKK3, the product of the MKK6 gene that we have previously shown to be the dominant activator of SAPK2 in extracts prepared from monocytes and muscle, as well as epithelial cells (Cuenda et al, 1996). SKK3 activated SAPK3 and SAPK2 at similar rates in vitro. Moreover, the stress-induced activation of SAPK3 was greatly enhanced by coexpression with SKK3. These observations indicate that SKK3 mediates the activation of SAPK3 by cellular stresses and cytokines in epithelial cells. SAPK3 was not activated at a significant rate by MKK1, SKK1 (MKK4), SAPKK2 (MKK3), SAPKK4 or SAPKK5.

Although the amino acid sequence of SAPK3 is 60% identical to SAPK2, and both enzymes share the TGY phosphorylation motif and a six amino acid acid insertion between subdomain VII and the activation loop in subdomain VIII, the properties of SAPK3 differed from SAPK2 in several respects. Firstly, SAPK3 was not inhibited by SB 203580 (FIG. 19). Secondly, SAPK3 but not SAPK2, phosphorylated ATF2 at Ser-90 (FIG. 17). Thirdly, SAPK3 was far less effective than SAPK2 in activating MAPKAP-K2 and MAPKAP-K3, consistent with the finding that SB 203580 suppresses the stress and cytokine-induced activation of MAPKAP-K2 and MAPKAP-K3 by 80–95% in every mammalian cell examined so far (Cuenda et al, 1995; Beyaert et al, 1996; Clifton et al, 1996; McLaughlin et al, 1996).

Despite the differences between SAPK3 and SAPK2 outlined above, these enzymes phosphorylated a number of proteins in vitro at similar rates (Table 1), including the transcription factor ATF2. ATF2 has been suggested to be a physiogical substrate of SAPK1 and SAPK2, since it is phosphorylated in cells cotransfected with SKK1, MEKK (an upstream activator of SKK1), or SKK3. However, transfection with upstream activators may not mimic the in vivo situation, for example by generating abnormally high levels of SAPK1 and SAPK2 activity. Moreover, the present work has raised another problem in the interpretation of these experiments by demonstrating that SKK3 activates SAPK3 as well as SAPK2. Further experiments employing SB 203580 are therefore essential to evaluate whether SAPK2 or SAPK3 mediates the phosphorylation of ATF2 triggered by transfection with SKK3. However, even if SB 203580 prevents the phosphorylation of ATF2 induced by transfection with SKK3, it is unlikely that SAPK2 activity is rate-limiting for ATF2 phosphorylation in vivo, because neither the TNF-induced (Beyaert et al, 1996) nor the stress-induced (Hazzalin et al, 1996) phosphorylation of the endogenous ATF2 in fibroblastic cell lines is affected by SB 203580 under conditions where this drug prevents the activation of MAPKAP-K2 and the induction of IL6 and c-fos mRNA. Further work is needed to clarify whether the phosphorylation of ATF2 occurring under these conditions is catalysed by SAPK1, SAPK3 or another (as yet unidentified) SAPK.

SAPK3 and SAPK2 phosphorylated the transcription factor Elk1 at similar rates (Table 2) and, like ATF2, Elk1 has been suggested to be a physiogical substrate of SAPK1 and SAPK2, because it becomes phosphorylated in cells that have been cotransfected with SKK1, MEKK or SKK3 (see Introduction). These experiments are subject to the same reservations as outlined above for ATF2, but a further caveat with Elk1 is that it is also an effective substrate for p42 and p44 MAP kinases which are activated by several of the stresses and cytokines that activate SAPKs. Elk1 (like SAP1 and SAP2) is an Ets domain protein and a member of the TCF family of transcription factors that form ternary complexes with the serum response factor (SRF) and bind to the serum response element (SRE) found in the promoters of a number of genes including c-Fos. The induction of c-fos mRNA in response to anisomycin or UV irradiation is largely suppressed by SB 203580 in C3H T101/2 fibroblasts (Hazzalin et al, 1996), while in HeLa cells and NIH 3T3 cells the induction of c-fos induced by UV irradiation was partially inhibited by SB 203580, partially inhibited by PD 98059 (a specific inhibitor of the activation of MKK1 (Alessi et al, 1995a)) and almost completely suppressed in the presence of both inhibitors (Price and Treisman, 1996). These observations demonstrate that SAPK2 activity is rate-limiting in the transcriptional activation of the c-fos gene and that the activation of both SAPK2 and ERK1/ERK2 contributes to the induction of c-fos mRNA in UV-irradiated cells. However, whether the suppression of c-fos mRNA production by SB 203580 results from inhibition of the phosphorylation of Elk1 or another TCF like SAP1 or SAP2, or by preventing the MAPKAP-K2-mediated phosphorylation of CREB (see Introduction), has not yet been established. The phosphorylation of Elk1 induced by cotransfection with MEKK was prevented by PD 98059, indicating that ERK1/ERK2 mediate the phosphorylation of Elk1 under these conditions. Earlier reports had claimed that SAPK1 was activated specifically when cells were transfected with low levels of MEKK DNA (Minden et al, 1994), but the effects of PD 98059 (which has no effect on the activation of SAPK1; Cuenda et al, 1995; Price and Treisman, 1996) indicate that this is not the case. Taken together, the results of Price and Treisman (1996) indicate that neither SAPK1 nor SAPK3 are rate-limiting for the phosphorylation of Elk1 and induction of c-fos mRNA in UV-irradiated HeLa cells.

Modifications and improvements may be incorporated without departing from the scope of the invention.

Table 2. Comparison of substrate specificities of SAPK2 and SAPK3. SAPK2 and SAPK3 were activated in vitro (FIG. 15) and phosphorylation of each protein studied at a SAPK concentration of 0.1 U/ml.

| Substrate | Rate of phosphorylation relative to MBP | |
|---|---|---|
| (1 $\mu$M) | SAPK2 | SAPK3 |
| MBP | 100 | 100 |
| Elk-1 | 122 ± 22 | 181 ± 30 |
| SAP1 | 55 ± 13 | 108 ± 15 |
| ATF2 | 86 ± 20 | 107 ± 20 |
| p53 | 13 ± 2 | 30 ± 1 |
| SAP2 | 13 ± 3 | 20 ± 3 |
| c-jun | 2 ± 1 | 2 ± 1 |

REFERENCES

Abe, J. I. et al (1996) "Big Mitogen-activated protein kinase-1 (BMK1) is a redox-sensitive kinase" *J. Biol. Chem.* 271, 16586–16590.
Alessi, D. R. et al (1995a) "PD 098059 is a specific inhibitor of the activation of mitogen-activated protein kinase kinase in vitro and in vivo" *J. Biol. Chem.* 270, 27489–27494.
Alessi, D. R. et al (1995b) *Methods Enzymol.* 255, 279–290.
Alessi, D. R. et al (1996) *EMBO J.* 15(23), 6541–6551.
Ben-Levy, R. et al (1995) *EMBO J.* 14, 101–110.
Beyaert, R. et al (1996) "The p38/RK mitogen-activated protein kinase pathway regulates interleukin-6 synthesis in response to tumour necrosis factor" *EMBO J.* 15, 1914–1923.
Blank, J. L. et al (1996) *J. Biol. Chem.* 271, 5361–5368.
Bradford, M. M. (1976) *Anal. Biochem.* 72, 248–254.
Brewster, J. L. et al (1993) "An osmosensing signal transduction pathway in yeast" *Science* 259, 1760–1763.
Cavigelli, M. et al (1995) *EMBO J.* 14, 5957–5964.
Clifton, A. D. et al (1996) "A comparison of the substrate specificity of MAPKAP kinase-2 and MAPKAP kinase-3 and their activation by cytokines and cellular stress" *FEBS Lett.* 392, 209–214.
Cohen, P. (1997) "Functions of mitogen- and stress-activated protein kinase cascades in mammalian cells identified by the use of specific inhibitors" *Trends Cell Biol.*, 7, 353.
Cuenda, A. et al (1995) "SB 203580 is a specific inhibitor of a MAP kinase homologue which is stimulated by cellular stresses and interleukin- 1" *FEBS Lett.* 364, 229–233.
Cuenda, A. et al (1996) "Purification and cDNA cloning of SKK3, the major activator of RK/p38 in stress- and cytokine-stimulated monocytes and epithelial cells" *EMBO J.* 15, 4156–4164.
Cuenda, A. et al (1997) "Activation of stress-activated protein kinase-3 (SAPK3) by cytokines and cellular stresses is mediated via SKK3 (MKK6); comparison of the specificities of SAPK3 and SAPK2 (RK/p38)" *EMBO J.* 16, 295–305.
Dérijard, B. et al (1994) "JNK1: a protein kinase stimulated by UV light and Ha-Ras that binds and phosphorylates the c-Jun activation domain" *Cell* 76, 1025–1037.
Dérijard, B. et al (1995) "Independent human MAP kinase signal transduction pathways defined by MEK and MKK isoforms" *Science* 267, 682–684.
Doza, Y. N. et al (1995) "Activation of the MAP kinase homologue RK requires the phosphorylation of Thr-180 and Tyr-182 and both residues are phosphorylated in chemically stressed KB cells" *FEBS Lett.* 364, 223–228.
Freshney, N. W. et al (1994) "Interleukin-1 activates a novel protein kinase cascade that results in the phosphorylation of hsp27" *Cell* 78, 1039–1049.

Fukunaga, R. and Hunter, T. (1997) "Mnk1, a new MAP kinase-activated protein kinase, isolated by a novel expression screening method for identifying protein kinase substrates" *EMBO J.* 16, in press.

Ginty, D. D. et al (1994) "Nerve growth factor activates a Ras-ependent protein kinase that stimulates c-fos transcription via phosphorylation of CREB" *Cell* 77, 713–725.

Goedert, M. et al (1997) "Assignment of the human stress-activated protein kinase-3 gene (SAPK3) to chromosome 22ql3.3 by fluorescence in situ hybridization" *Genomics*, in press.

Gould, G. W. et al (1995) "The activation of distinct mitogen-activated protein kinase cascades is required for the stimulation of 2-deoxyglucose uptake by interleukin-1 and insulin-like growth factor-1 in KB cells" *Biochem. J.* 311,735–738.

Gupta, S. et al (1995) "Transcription factor ATF2 regulation by the JNK signal transduction pathway" *Science* 267, 389–393.

Han, J. et al (1994) "A MAP kinase targeted by endotoxin and hyperosmolarity in mammalian cells" *Science* 265, 808–811.

Han, J. et al (1996) "Characterization of the structure and function of a novel MAP kinase kinase (MKK6)" *J. Biol. Chem.* 271, 2886–2891.

Hazzalin, C. A. (1996) "Essential role for p38/RK in stress-induced nuclear responses" *Curr. Biol.* 6, 1028–1031.

Helps, N. R. et al (1995) *FEBS Lett.* 377, 295–300.

Hibi, M. et al (1993) "Identification of an oncoprotein- and UV-responsive protein kinase that binds and potentiates the c-Jun activation domain" *Genes Dev.* 7, 2135–2148.

Hirai, S. I. et al (1996) *Oncogene* 12, 641–650.

Huot, J. et al (1995) "Characterization of 45-kDa/54-kDa HSP27 kinase, a stress-sensitive kinase which may activate the phosphorylation-dependent protective function of mammalian 27-kDa heat shock protein HSP27" *Eur. J. Biochem.* 227,416427.

Jiang, Y. et al (1996) "Characterization of the structure and function of a new mitogen-activated protein kinase (p38p)" *J. Biol. Chem.* 271, 17920–17926.

Kyriakis, J. M. (1994) "The stress-activated protein kinase subfamily of c-Jun kinases" *Nature* 369, 156–160.

Lavoie, J. N. et al (1995) *Mol. Cell Biol.* 15, 505–516.

Lechner, C. (1996) "ERK6, a mitogen-activated protein kinase involved in C2C12 myoblast differentiation" *Proc. Natl. Acad. Sci. USA* 93,4355–4359.

Lee, J. C. et al (1994) "A protein kinase involved in the regulation of inflammatory cytokine biosynthesis" *Nature* 372, 739–746.

Lee, J. D. et al (1995) "Primary structure of BMK1: a new mammalian MAP kinase" *Biochem. Biophys. Res. Commun.* 213, 715–724.

Li, Z. et al (1996) "The primary structure of p38: a new member of p38 group of MAP kinases" *Biochem. Biophys. Res. Commun.* 228, 334–340.

Lin, A. et al (1995) *Science* 268, 286–290.

Livingstone, C. et al (1995) *J. Biol. Chem.* 270, 12781–12786.

McLaughlin, M. M. et al (1996) "Identification of mitogen-activated protein (MAP) kinase-activated protein kinase-3, a novel substrate of CSBP p38 MAP kinase" *J. Biol. Chem.* 271, 8488–8492.

Meier, R. et al (1996) "Cellular stresses and cytokines activate multiple mitogen-activated protein kinase kinase homologues in PC12 and KB cells" *Eur. J. Biochem.* 236, 796–805.

Mertens, S. et al (1996) "SAP kinase-3, a new member of the family of mammalian stress-activated protein kinases" *FEBS Lett.* 383, 273–276.

Minden, A. et al (1994) *Science* 266, 1719–1723.

Moriguchi, T. et al (1996) "A novel kinase cascade mediated by mitogen-activated protein kinase kinase 6 and MKK3" *J. Biol. Chem.* 271,13675–13679.

Olson, N. F. et al (1995) *Science* 269, 1270–1272.

Paul, A. et al (1996)

Price, M. A. et al (1996) "The p38 and ERK MAP kinase pathways cooperate to activate Ternary Complex Factors and c-fos transcription in response to UV light" *EMBO J.* 15, 6552–6563.

Pulverer, B. J. et al (1991) "Phosphorylation of c-jun mediated by MAP kinases" *Nature* 353, 670–674.

Raingeaud, J. et al (1996) "MKK3-and MKK6-regulated gene expression is mediated by the p38 mitogen-activated protein kinase signal transduction pathway" *Mol. Cell. Biol.* 16, 1247–1255.

Rana, A. et al (1996) *J. Biol. Chem.* 271, 19025–19028.

Rouse, J. et al (1994) "A novel kinase cascade triggered by stress and heat shock that stimulates MAPKAP kinase-2 and phosphorylation of the small heat shock proteins" *Cell* 78, 1027–1037.

Saklatvala, J. et al (1996) "Role of p38 mitogen-activated protein kinase in platelet aggregation caused by collagen or a thromboxane analogue" *J. Biol. Chem.* 271, 6586–6589.

Salmeron, A. et al (1996) *EMBO J.* 15, 817–826.

Sanchez, I. et al (1994) "Role of SAPK/ERK kinase-1 in the stress-activated pathway regulating transcription factor c-Jun" *Nature* 372, 79414 798.

Sithanandam, G. et al (1996) "3pK, a new MAP kinase activated protein kinase, located in the small cell lung cancer tumour suppressor gene region" *Mol. Cell. Biol.* 16, 868–876.

Stein, B. et al (1996) "Cloning and characterisation of MEK6, a novel member of the mitogen-activated protein kinase kinase cascade" *J. Biol. Chem.* 271, 11427–11433.

Stokoe, D. et al (1992a) *FEBS Lett* 313, 307–313.

Stokoe, D. et al (1992b) "MAPKAP kinase-2; a novel protein kinase activated by mitogen-activated protein kinase" *EMBO J.* 11, 3985–3994.

Stokoe, D. et al (1993) *Biochem. J.* 296, 843–849.

Tan, Y. et al (1996) "FGF and stress regulate CREB and ATF-1 via a pathway involving p38 MAP kinase and MAPKAP kinase-2" *EMBO J.* 15,4629–4642.

Wang, X. Z. and Ron D. (1996) "Stress-induced phosphorylation and activation of the transcription factor CHOP (GADD153) by p38 MAP kinase" *Science* 272, 1347–1348.

Waskiewicz, A. J. et al (1997) "Mitogen-activated protein kinases activate the serine/threonine kinases Mnk1 and Mnk2" *EMBO J.* 16, 1909–1920.

Whitmarsh, A. J. et al (1995) *Science* 269, 403407.

Xu, S. et al (1996) *PNAS USA* 93, 5291–5295.

Yan, M. et al (1994) "Activation of stress-activated protein kinase by MEKK1 phosphorylation of its activator SEK1" *Nature* 372, 798–800.

Yashar, B. M. et al (1993) "Novel members of the mitogen-activated protein kinase activator family in *Xenopus laevis*" *Mol. Cell. Biol.* 13, 5738–5748.

Zervos, A. S. et al (1995) "Mxi2, a mitogen-activated protein kinase that recognizes and phosphorylates Max protein" *Proc. Natl. Acad. Sci. USA* 92, 10531–10534.

Zhou, G. et al (1995) "Components of a new human protein kinase signal transduction pathway" *J. Biol. Chem.* 270, 12665–12669.

Zinck, R. et al (1995) *Mol. Cell. Biol.* 15, 4930–4938.

What is claimed is:

1. A method of identifying a compound which blocks the activation of a stress-activated protein kinase selected from the group consisting of SAPK4, SAPK3/ERK6/p38γ, variants thereof having at least 80% identity with SAPK4 or SAPK3/ERK6/p38γ, and fusions thereof by SKK3/MKK6/MEK6, the method comprising:

contacting the stress-activated protein kinase with the compound and determining whether the compound enhances or disrupts the interaction between said stress-activated protein kinase and SKK3/MKK6/MEK6.

2. The method according to claim 1 wherein the SKK3/MKK6/MEK6 is purified before being contacted with the stress-activated protein kinase.

3. A method of identifying a compound which blocks the activation of a stress-activated protein kinase selected from the group consisting of SAPK4, SAPK3/ERK6/p38γ, variants thereof having at least 80% identity with SAPK4 or SAPK3/ERK6/p38γ, and fusions thereof by SKK3/MKK6/MEK6, the method comprising:
  contacting the stress-activated protein kinase with the compound and
  determining whether the compound blocks activation of the stress-activated protein kinase by SKK3/MKK6/MEK6 wherein the variants thereof having at least 80% identity with SAPK4 or SAPK3/ERK6/p38γ or fusion thereof is capable of phosphorylating myelin basic protein and is not inhibited by SB 203 580 or SB 202 190 and has the amino acid sequence TGY in the activation domain.

4. A kit for screening for compounds which block the activation of a stress activated protein kinase by SKK3/MKK6/MEK6, the kit comprising:
  (i) a stress activated protein kinase selected from the group consisting of SAPK4, SAPK3/ERK6/p38γ, variants thereof having at least 80% identity with SAPK4 or SAPK3/ERK6/p38γ, and fusions thereof; and
  (ii) SKK3/MKK6/MEK6.

5. A method of identifying agents able to influence the activity of a stress-activated protein kinase selected from the group consisting of SAPK4 and SAPK3/ERK6/p38γ, said method comprising:
  contacting the stress-activated protein to SKK3/MKK6/MEK6;
  contacting a test substance to the stress-activated protein kinase in the presence of a substrate for the stress-activated protein kinase; and
  detecting whether said substrate has been phosphorylated.

6. The method according to claim 5, wherein the substrate comprises myelin basic protein, a transcription factor, a test substance or a phosphatase which is itself capable of affecting protein phosphorylation, gene expression and/or protein synthesis.

7. The method according to claim 6, wherein the transcription factor is ATF-2.

8. A method of activating a stress-activated protein kinase selected from the group consisting of SAPK4, SAPK3/ERK6/p38γ, variants thereof having at least 80% identity with SAPK4 or SAPK3/ERK6/p38γ, and fusions thereof, said method comprising:
  incubating the stress-activated protein kinase with SKK3/MKK6/MEK6, wherein the SKK3/MKK6/MEK6 is purified.

9. The method according to claim 5, wherein the stress-activated protein kinase is SAPK4.

10. The method according to claim 5, wherein the stress-activated protein kinase is SAPK3/ERK6/p38γ.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 365 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met Ser Leu Ile Arg Lys Lys Gly Phe Tyr Lys Gln Asp Val Asn Lys
  1               5                  10                  15

Thr Ala Trp Glu Leu Pro Lys Thr Tyr Val Ser Pro Thr His Val Gly
             20                  25                  30

Ser Gly Ala Tyr Gly Ser Val Cys Ser Ala Ile Asp Lys Arg Ser Gly
         35                  40                  45

Glu Lys Val Ala Ile Lys Lys Leu Ser Arg Pro Phe Gln Ser Glu Ile
 50                  55                  60

Phe Ala Lys Arg Ala Tyr Arg Glu Leu Leu Leu Lys His Met Gln
 65                  70                  75                  80

His Glu Asn Val Ile Gly Leu Leu Asp Val Phe Thr Pro Ala Ser Ser
                     85                  90                  95

Leu Arg Asn Phe Tyr Asp Phe Tyr Leu Val Met Pro Phe Met Gln Thr
                100                 105                 110

Asp Leu Gln Lys Ile Met Gly Met Glu Phe Ser Glu Glu Lys Ile Gln
                115                 120                 125

Tyr Leu Val Tyr Gln Met Leu Lys Gly Leu Lys Tyr Ile His Ser Ala
                130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
                180                 185                 190

Val Ile Leu Ser Trp Met His Tyr Asn Gln Thr Val Asp Ile Trp Ser
                195                 200                 205

Val Gly Cys Ile Met Ala Glu Met Leu Thr Gly Lys Thr Leu Phe Lys
                210                 215                 220

Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
                245                 250                 255

Ser Tyr Ile Gln Ser Leu Pro Gln Thr Pro Arg Lys Asp Phe Thr Gln
                260                 265                 270

Leu Phe Pro Arg Ala Ser Pro Gln Ala Ala Asp Leu Leu Glu Lys Met
                275                 280                 285

Leu Glu Leu Asp Val Asp Lys Arg Leu Thr Ala Ala Gln Ala Leu Thr
                290                 295                 300

His Pro Phe Phe Glu Pro Phe Arg Asp Pro Glu Glu Thr Glu Ala
305                 310                 315                 320
```

```
Gln Gln Pro Phe Asp Asp Ser Leu Glu His Glu Lys Leu Thr Val Asp
            325                 330                 335

Glu Trp Lys Gln His Ile Tyr Lys Glu Ile Val Asn Phe Ser Pro Ile
            340                 345                 350

Ala Arg Lys Asp Ser Arg Arg Arg Ser Gly Met Lys Leu
            355                 360                 365

(2) INFORMATION FOR SEQ ID NO: 2:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 2:

ATGAGCCTCA TCCGGAAAAA GGGCTTCTAC AAGCAGGACG TCAACAAGAC CGCCTGGGAG      60

CTGCCCAAGA CCTACGTGTC CCCGACGCAC GTCGGCAGCG GGGCCTATGG CTCCGTGTGC     120

TCGGCCATCG ACAAGCGGTC AGGGGAGAAG GTGGCCATCA AGAAGCTGAG CCGACCCTTT     180

CAGTCCGAGA TCTTCGCCAA GCGCGCCTAC CGGGAGCTGC TGCTGCTGAA GCACATGCAG     240

CATGAGAACG TCATTGGGCT CCTGGATGTC TTCACCCCAG CCTCCTCCCT GCGCAACTTC     300

TATGACTTCT ACCTGGTGAT GCCCTTCATG CAGACGGATC TGCAGAAGAT CATGGGGATG     360

GAGTTCAGTG AGGAGAAGAT CCAGTACCTG GTGTATCAGA TGCTCAAAGG CCTTAAGTAC     420

ATCCACTCTG CTGGGGTCGT GCACAGGGAC CTGAAGCCAG CAACCTGGC TGTGAATGAG      480

GACTGTGAAC TGAAGATTCT GGATTTTGGG CTGGCGCGAC ATGCAGACGC CGAGATGACT     540

GGCTACGTGG TGACCCGCTG GTACCGAGCC CCGAGGTGA TCCTCAGCTG GATGCACTAC      600

AACCAGACAG TGGACATCTG GTCTGTGGGC TGTATCATGG CAGAGATGCT GACAGGGAAA     660

ACTCTGTTCA AGGGGAAAGA TTACCTGGAC CAGCTGACCC AGATCCTGAA AGTGACCGGG     720

GTGCCTGGCA CGGAGTTTGT GCAGAAGCTG AACGACAAAG CGGCCAAATC CTACATCCAG     780

TCCCTGCCAC AGACCCCCAG GAAGGATTTC ACTCAGCTGT TCCCACGGGC CAGCCCCCAG     840

GCTGCGGACC TGCTGGAGAA GATGCTGGAG CTAGACGTGG ACAAGCGCCT GACGGCCGCG     900

CAGGCCCTCA CCCATCCCTT CTTTGAACCC TTCCGGGACC CTGAGGAAGA CGGAGGCC      960

CAGCAGCCGT TTGATGATTC CTTAGAACAC GAGAAACTCA CAGTGGATGA ATGGAAGCAG    1020

CACATCTACA AGGAGATTGT GAACTTCAGC CCCATTGCCC GGAAGGACTC ACGGCGCCGG    1080

AGTGGCATGA AGCTG                                                    1095

(2) INFORMATION FOR SEQ ID NO: 3:

(i) SEQUENCE CHARACTERISTICS:
        (A) LENGTH: 1259 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 3:

CCGCCGAGAT CGGGTGCCCG GGATGAGCCT CATCCGGAAA AAGGGCTTCT ACAAGCAGGA      60

CGTCAACAAG ACCGCCTGGG AGCTGCCCAA GACCTACGTG TCCCCGACGC ACGTCGGCAG     120

CGGGGCCTAT GGCTCCGTGT GCTCGGCCAT CGACAAGCGG TCAGGGGAGA AGGTGGCCAT     180
```

```
CAAGAAGCTG AGCCGACCCT TTCAGTCCGA GATCTTCGCC AAGCGCGCCT ACCGGGAGCT       240

GCTGCTGCTG AAGCACATGC AGCATGAGAA CGTCATTGGG CTCCTGGATG TCTTCACCCC       300

AGCCTCCTCC CTGCGCAACT TCTATGACTT CTACCTGGTG ATGCCCTTCA TGCAGACGGA       360

TCTGCAGAAG ATCATGGGGA TGGAGTTCAG TGAGGAGAAG ATCCAGTACC TGGTGTATCA       420

GATGCTCAAA GGCCTTAAGT ACATCCACTC TGCTGGGGTC GTGCACAGGG ACCTGAAGCC       480

AGGCAACCTG GCTGTGAATG AGGACTGTGA ACTGAAGATT CTGGATTTTG GGCTGGCGCG       540

ACATGCAGAC GCCGAGATGA CTGGCTACGT GGTGACCCCC TGGTACCGAG CCCCCGAGGT       600

GATCCTCAGC TGGATGCACT ACAACCAGAC AGTGGACATC TGGTCTGTGG GCTGTATCAT       660

GGCAGAGATG CTGACAGGGA AAACTCTGTT CAAGGGGAAA GATTACCTGG ACCAGCTGAC       720

CCAGATCCTG AAAGTGACCG GGGTGCCTGG CACGGAGTTT GTGCAGAAGC TGAACGACAA       780

AGCGGCCAAA TCCTACATCC AGTCCCTGCC ACAGACCCCC AGGAAGGATT TCACTCAGCT       840

GTTCCCACGG GCCAGCCCCC AGGCTGCGGA CCTGCTGGAG AAGATGCTGG AGCTAGACGT       900

GGACAAGCGC CTGACGGCCG CGCAGGCCCT CACCCATCCC TTCTTTGAAC CCTTCCGGGA       960

CCCTGACGAA GAGACGGAGG CCCAGCAGCC GTTTGATGAT TCCTTAGAAC ACGAGAAACT      1020

CACAGTGGAT GAATGGAAGC AGCACATCTA CAAGGAGATT GTGAACTTCA GCCCCATTGC      1080

CCGGAAGGAC TCACGGCGCC GGAGTGGCAT GAAGCTGTAG GGACTCATCT TGCATGGCAC      1140

CGCCGGCCAG ACACTGCCCA AGGACCAGTA TTTGTCACTA CCAAACTCAG CCCTTCTTGG      1200

AATACAGCCT TTCAAGCAGA GGACAGAAGG GTCCTTCTCC TTATGTGGGA AATGGGCCT      1259

(2) INFORMATION FOR SEQ ID NO: 4:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Met Glu Gln Lys Leu Ile Ser Glu Glu Asp Leu Asn
1               5                   10

(2) INFORMATION FOR SEQ ID NO: 5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Lys Pro Pro Arg Asn Leu Gly Ala Arg Val Pro Lys Glu Thr Ala Leu
1               5                   10                  15
```